United States Patent
Stack et al.

(10) Patent No.: US 8,206,456 B2
(45) Date of Patent: *Jun. 26, 2012

(54) RESTRICTIVE AND/OR OBSTRUCTIVE IMPLANT SYSTEM FOR INDUCING WEIGHT LOSS

(75) Inventors: Richard S. Stack, Chapel Hill, NC (US); Daniel J. Balbierz, Redwood City, CA (US); William L. Athas, Durham, NC (US); John Lunsford, San Carlos, CA (US); Kevin van Bladel, Livermore, CA (US); Ashik Mohan, Petaluma, CA (US); Samuel T. Crews, Woodside, CA (US); Shuji Uemura, San Francisco, CA (US); Robert H. Hawes, Awendaw, SC (US)

(73) Assignee: Barosense, Inc., Redwood City, CA (US)

( * ) Notice: Subject to any disclaimer, the term of this patent is extended or adjusted under 35 U.S.C. 154(b) by 881 days.

This patent is subject to a terminal disclaimer.

(21) Appl. No.: 11/439,461

(22) Filed: May 23, 2006

(65) Prior Publication Data

US 2008/0065122 A1   Mar. 13, 2008

Related U.S. Application Data

(63) Continuation-in-part of application No. 10/575,222, filed on Jul. 30, 2007, which is a continuation of application No. PCT/US2004/033007, filed on Oct. 8, 2004, which is a continuation-in-part of application No. 10/843,702, filed on May 11, 2004, now abandoned, application No. 11/439,461, which is a continuation-in-part of application No. 10/898,036, filed on Jul. 23, 2004, now Pat. No. 7,431,725.

(60) Provisional application No. 60/683,635, filed on May 23, 2005, provisional application No. 60/510,268, filed on Oct. 10, 2003.

(51) Int. Cl.
*A61F 2/02* (2006.01)

(52) U.S. Cl. ...................................................... 623/23.65

(58) Field of Classification Search ....... 623/23.64–23.67
See application file for complete search history.

(56) References Cited

U.S. PATENT DOCUMENTS 1,408,865 A   3/1922   Codwell
(Continued)

FOREIGN PATENT DOCUMENTS

CH          680263 A5     7/1992
(Continued)

OTHER PUBLICATIONS

Felsher et al., "Mucosal Apposition in Endoscopic Suturing", *Gatrointestinal Endoscopy*, 58(6):867-870 (2003).

(Continued)

*Primary Examiner* — Ryan Severson
(74) *Attorney, Agent, or Firm* — King & Spalding LLP; Peter J. Dehlinger; Kathleen A. Frost

(57) ABSTRACT

The present application describes an implant system useable for positioning an implant device such as a device useful for restricting passage of ingested food into the stomach. In one embodiment, the disclosed system includes a plurality of anchors that may be coupled to tissue within the stomach, or to a tissue tunnel formed by plicating stomach wall tissue. The anchor includes a loop. During use, the implant device is inserted through the loop and expanded such that it retains its position within the loop until removed. Instruments for implanting and explanting the implant device are also described.

4 Claims, 18 Drawing Sheets

U.S. PATENT DOCUMENTS

| | | |
|---|---|---|
| 3,663,965 A | 5/1972 | Lee et al. |
| 4,134,405 A | 1/1979 | Smit |
| 4,207,890 A | 6/1980 | Mamajek et al. |
| 4,246,893 A | 1/1981 | Berson |
| 4,315,509 A | 2/1982 | Smit |
| 4,331,277 A | 5/1982 | Green |
| 4,403,604 A | 9/1983 | Wilkinson et al. |
| 4,416,267 A | 11/1983 | Garren et al. |
| 4,417,360 A | 11/1983 | Moasser |
| 4,441,215 A | 4/1984 | Kaster |
| 4,467,804 A | 8/1984 | Hardy et al. |
| 4,485,805 A | 12/1984 | Foster, Jr. |
| 4,501,264 A | 2/1985 | Rockey |
| 4,607,618 A | 8/1986 | Angelchik |
| 4,617,932 A | 10/1986 | Kornberg |
| 4,641,653 A | 2/1987 | Rockey |
| 4,648,383 A | 3/1987 | Angelchik |
| 4,694,827 A | 9/1987 | Weiner et al. |
| 4,723,547 A | 2/1988 | Kullas et al. |
| 4,747,849 A | 5/1988 | Galtier |
| 4,846,836 A | 7/1989 | Reich |
| 4,848,367 A | 7/1989 | Avant et al. |
| 4,899,747 A | 2/1990 | Garren et al. |
| 4,925,446 A | 5/1990 | Garay et al. |
| 4,946,440 A | 8/1990 | Hall |
| 4,969,896 A | 11/1990 | Shors |
| 4,997,084 A | 3/1991 | Opie et al. |
| 5,006,106 A | 4/1991 | Angelchik |
| 5,037,021 A | 8/1991 | Mills et al. |
| 5,061,275 A | 10/1991 | Wallsten et al. |
| 5,084,061 A | 1/1992 | Gau et al. |
| 5,088,979 A | 2/1992 | Filipi et al. |
| 5,163,952 A | 11/1992 | Froix |
| 5,211,658 A | 5/1993 | Clouse |
| 5,234,454 A | 8/1993 | Bangs |
| 5,246,456 A | 9/1993 | Wilkinson |
| 5,259,399 A | 11/1993 | Brown |
| 5,263,629 A | 11/1993 | Trumbull et al. |
| 5,290,217 A | 3/1994 | Campos |
| 5,306,300 A | 4/1994 | Berry |
| 5,314,473 A | 5/1994 | Godin |
| 5,327,914 A | 7/1994 | Shlain |
| 5,345,949 A | 9/1994 | Shlain |
| 5,355,897 A | 10/1994 | Pietrafitta et al. |
| 5,401,241 A | 3/1995 | Delany |
| 5,403,326 A | 4/1995 | Harrison et al. |
| 5,405,377 A | 4/1995 | Cragg |
| 5,431,673 A | 7/1995 | Summers et al. |
| 5,486,187 A | 1/1996 | Schenck |
| 5,514,167 A | 5/1996 | Smith et al. |
| 5,535,935 A | 7/1996 | Vidal et al. |
| 5,542,949 A | 8/1996 | Yoon |
| 5,562,239 A | 10/1996 | Boiarski et al. |
| 5,571,116 A | 11/1996 | Bolanos et al. |
| 5,577,654 A | 11/1996 | Bishop |
| 5,593,434 A | 1/1997 | Williams |
| 5,597,107 A | 1/1997 | Knodel et al. |
| 5,609,624 A | 3/1997 | Kalis |
| 5,628,786 A | 5/1997 | Banas et al. |
| 5,630,539 A | 5/1997 | Plyley et al. |
| 5,647,526 A | 7/1997 | Green et al. |
| 5,653,743 A | 8/1997 | Martin |
| 5,662,713 A | 9/1997 | Andersen et al. |
| 5,673,841 A | 10/1997 | Schulze et al. |
| 5,674,241 A | 10/1997 | Bley et al. |
| 5,706,998 A | 1/1998 | Plyley et al. |
| 5,709,657 A | 1/1998 | Zimmon |
| 5,720,776 A | 2/1998 | Chuter et al. |
| 5,749,918 A | 5/1998 | Hogendijk et al. |
| 5,762,255 A | 6/1998 | Chrisman et al. |
| 5,771,903 A | 6/1998 | Jakobsson |
| 5,785,684 A | 7/1998 | Zimmon |
| 5,792,119 A | 8/1998 | Marx |
| 5,820,584 A | 10/1998 | Crabb |
| 5,839,639 A | 11/1998 | Sauer et al. |
| 5,848,964 A | 12/1998 | Samuels |
| 5,855,311 A | 1/1999 | Hamblin et al. |
| 5,855,601 A | 1/1999 | Bessler et al. |
| 5,856,445 A | 1/1999 | Korsmeyer |
| 5,861,036 A | 1/1999 | Godin |
| 5,868,141 A | 2/1999 | Ellias |
| 5,887,594 A | 3/1999 | LoCicero, III |
| 5,897,562 A | 4/1999 | Bolanos et al. |
| 5,910,144 A | 6/1999 | Hayashi et al. |
| 5,922,019 A | 7/1999 | Hankh et al. |
| 5,947,983 A | 9/1999 | Solar et al. |
| 5,993,473 A | 11/1999 | Chan et al. |
| 5,993,483 A | 11/1999 | Gianotti |
| 6,016,848 A | 1/2000 | Egrees |
| 6,051,015 A | 4/2000 | Maahs |
| 6,086,600 A | 7/2000 | Kortenbach |
| 6,098,629 A | 8/2000 | Johnson et al. |
| 6,102,922 A | 8/2000 | Jakobsson et al. |
| 6,113,609 A | 9/2000 | Adams |
| 6,120,534 A | 9/2000 | Ruiz |
| 6,146,416 A | 11/2000 | Andersen et al. |
| 6,159,146 A | 12/2000 | El Gazayerli |
| 6,159,238 A | 12/2000 | Killion et al. |
| 6,197,022 B1 | 3/2001 | Baker |
| 6,206,930 B1 | 3/2001 | Burg et al. |
| 6,245,088 B1 | 6/2001 | Lowery |
| 6,251,132 B1 | 6/2001 | Ravenscroft et al. |
| 6,254,642 B1 | 7/2001 | Taylor |
| 6,258,120 B1 | 7/2001 | McKenzie et al. |
| 6,264,700 B1 | 7/2001 | Kilcoyne et al. |
| 6,287,334 B1 | 9/2001 | Moll et al. |
| 6,302,917 B1 | 10/2001 | Dua et al. |
| 6,358,197 B1 | 3/2002 | Silverman |
| 6,416,522 B1 | 7/2002 | Strecker |
| 6,425,916 B1 | 7/2002 | Garrison et al. |
| 6,454,785 B2 | 9/2002 | De Hoyos Garza |
| 6,460,543 B1 | 10/2002 | Forsell |
| 6,461,366 B1 | 10/2002 | Seguin |
| 6,494,888 B1 | 12/2002 | Laufer et al. |
| 6,494,895 B2 | 12/2002 | Addis |
| 6,503,264 B1 | 1/2003 | Birk |
| 6,506,196 B1 | 1/2003 | Laufer |
| 6,527,784 B2 | 3/2003 | Adams et al. |
| 6,540,789 B1 | 4/2003 | Silverman et al. |
| 6,544,291 B2 | 4/2003 | Taylor |
| 6,547,801 B1 | 4/2003 | Dargent et al. |
| 6,558,400 B2 | 5/2003 | Deem et al. |
| 6,558,429 B2 | 5/2003 | Taylor |
| 6,572,627 B2 | 6/2003 | Gabbay |
| 6,572,629 B2 | 6/2003 | Kalloo |
| 6,575,896 B2 | 6/2003 | Silverman et al. |
| 6,592,596 B1 | 7/2003 | Geitz et al. |
| 6,596,023 B1 | 7/2003 | Nunez et al. |
| 6,607,555 B2 | 8/2003 | Patterson et al. |
| 6,627,206 B2 | 9/2003 | Lloyd |
| 6,632,227 B2 | 10/2003 | Adams |
| 6,663,639 B1 | 12/2003 | Laufer et al. |
| 6,675,809 B2 | 1/2004 | Stack et al. .................. 128/898 |
| 6,740,098 B2 | 5/2004 | Abrams et al. |
| 6,740,121 B2 | 5/2004 | Geitz |
| 6,746,460 B2 | 6/2004 | Gannoe et al. |
| 6,755,869 B2 | 6/2004 | Geitz |
| 6,764,518 B2 | 7/2004 | Godin |
| 6,773,440 B2 | 8/2004 | Gannoe et al. |
| 6,773,441 B1 | 8/2004 | Laufer et al. |
| 6,790,214 B2 | 9/2004 | Kraemer et al. |
| 6,790,237 B2 | 9/2004 | Stinson |
| 6,821,285 B2 | 11/2004 | Laufer et al. |
| 6,835,200 B2 | 12/2004 | Laufer et al. |
| 6,845,776 B2 | 1/2005 | Stack et al. .................. 128/898 |
| 6,916,332 B2 | 7/2005 | Adams |
| 6,932,838 B2 | 8/2005 | Schwartz et al. |
| 6,960,233 B1 | 11/2005 | Berg et al. |
| 6,966,875 B1 | 11/2005 | Longobardi |
| 6,981,978 B2 | 1/2006 | Gannoe |
| 6,981,980 B2 | 1/2006 | Sampson et al. |
| 6,994,715 B2 | 2/2006 | Gannoe et al. |
| 7,011,094 B2 | 3/2006 | Rapackie et al. |
| 7,020,531 B1 | 3/2006 | Colliou et al. |
| 7,025,791 B2 | 4/2006 | Levine et al. |
| 7,033,373 B2 | 4/2006 | de la Torre et al. |
| 7,033,384 B2 | 4/2006 | Gannoe et al. |

| | | |
|---|---|---|
| 7,037,344 B2 | 5/2006 | Kagan et al. |
| 7,146,984 B2 | 12/2006 | Stack et al. .................... 128/898 |
| 7,431,725 B2 | 10/2008 | Stack et al. |
| 7,744,627 B2 | 6/2010 | Orban, III et al. |
| 7,753,870 B2 | 7/2010 | Demarais et al. |
| 7,766,861 B2 | 8/2010 | Levine et al. |
| 7,837,669 B2 | 11/2010 | Dann et al. |
| 2001/0011543 A1 | 8/2001 | Forsell |
| 2001/0020189 A1 | 9/2001 | Taylor |
| 2001/0020190 A1 | 9/2001 | Taylor |
| 2001/0021796 A1 | 9/2001 | Silverman et al. |
| 2001/0044595 A1 | 11/2001 | Reydel et al. |
| 2002/0022851 A1 | 2/2002 | Kalloo et al. |
| 2002/0055757 A1 | 5/2002 | Torre et al. |
| 2002/0072761 A1 | 6/2002 | Abrams et al. |
| 2002/0082621 A1 | 6/2002 | Schurr et al. |
| 2002/0099439 A1 | 7/2002 | Schwartz et al. |
| 2002/0183767 A1 | 12/2002 | Adams et al. |
| 2002/0183768 A1 | 12/2002 | Deem et al. |
| 2003/0009236 A1 | 1/2003 | Godin |
| 2003/0040804 A1 | 2/2003 | Stack et al. .................... 128/898 |
| 2003/0040808 A1 | 2/2003 | Stack et al. .................... 128/898 |
| 2003/0065359 A1 | 4/2003 | Weller et al. |
| 2003/0093117 A1 | 5/2003 | Saadat |
| 2003/0109892 A1 | 6/2003 | Deem et al. |
| 2003/0120289 A1 | 6/2003 | McGuckin, Jr. et al. |
| 2003/0158569 A1 | 8/2003 | Wazne |
| 2003/0191476 A1 | 10/2003 | Smit |
| 2003/0199989 A1 | 10/2003 | Stack et al. |
| 2003/0199990 A1 | 10/2003 | Stack et al. |
| 2003/0199991 A1 | 10/2003 | Stack et al. ................. 623/23.65 |
| 2003/0208209 A1 | 11/2003 | Gambale et al. |
| 2003/0220660 A1 | 11/2003 | Kortenbach et al. |
| 2004/0006351 A1 | 1/2004 | Gannoe et al. |
| 2004/0024386 A1 | 2/2004 | Deem et al. |
| 2004/0030347 A1* | 2/2004 | Gannoe et al. ................ 606/153 |
| 2004/0044353 A1 | 3/2004 | Gannoe |
| 2004/0044354 A1 | 3/2004 | Gannoe et al. |
| 2004/0044357 A1 | 3/2004 | Gannoe et al. |
| 2004/0044364 A1 | 3/2004 | DeVries et al. |
| 2004/0059289 A1 | 3/2004 | Garza et al. |
| 2004/0068276 A1 | 4/2004 | Golden et al. |
| 2004/0082963 A1 | 4/2004 | Gannoe et al. |
| 2004/0088023 A1 | 5/2004 | Imran et al. |
| 2004/0092892 A1 | 5/2004 | Kagan et al. |
| 2004/0092974 A1 | 5/2004 | Gannoe et al. |
| 2004/0093091 A1 | 5/2004 | Gannoe et al. |
| 2004/0098043 A1 | 5/2004 | Trout |
| 2004/0107004 A1 | 6/2004 | Levine et al. |
| 2004/0117031 A1 | 6/2004 | Stack et al. ................. 623/23.65 |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0153167 A1 | 8/2004 | Stack et al. |
| 2004/0158331 A1 | 8/2004 | Stack et al. .................... 128/898 |
| 2004/0162568 A1 | 8/2004 | Saadat et al. |
| 2004/0172141 A1 | 9/2004 | Stack et al. |
| 2004/0172142 A1 | 9/2004 | Stack et al. |
| 2004/0186502 A1 | 9/2004 | Sampson et al. |
| 2004/0210243 A1 | 10/2004 | Gannoe et al. |
| 2004/0215216 A1 | 10/2004 | Gannoe et al. |
| 2004/0220682 A1 | 11/2004 | Levine et al. |
| 2004/0225183 A1 | 11/2004 | Michlitsch et al. |
| 2004/0225305 A1 | 11/2004 | Ewers et al. |
| 2004/0236419 A1 | 11/2004 | Milo ............................... 623/2.36 |
| 2004/0243152 A1 | 12/2004 | Taylor et al. |
| 2004/0243223 A1 | 12/2004 | Kraemer et al. |
| 2004/0267378 A1 | 12/2004 | Gazi et al. |
| 2005/0004430 A1 | 1/2005 | Lee et al. |
| 2005/0004681 A1 | 1/2005 | Stack et al. |
| 2005/0033326 A1 | 2/2005 | Briganti et al. |
| 2005/0033345 A1 | 2/2005 | DeLegge |
| 2005/0049718 A1 | 3/2005 | Dann et al. |
| 2005/0075654 A1 | 4/2005 | Kelleher |
| 2005/0080444 A1 | 4/2005 | Kraemer et al. |
| 2005/0085787 A1 | 4/2005 | Laufer et al. |
| 2005/0096673 A1 | 5/2005 | Stack et al. .................... 606/151 |
| 2005/0096750 A1 | 5/2005 | Kagan et al. |
| 2005/0149114 A1 | 7/2005 | Cartledge et al. |
| 2005/0159769 A1 | 7/2005 | Alverdy |
| 2005/0177181 A1 | 8/2005 | Kagan et al. |
| 2005/0183732 A1 | 8/2005 | Edwards |
| 2005/0192599 A1 | 9/2005 | Demarais |
| 2005/0192615 A1 | 9/2005 | Torre et al. |
| 2005/0216040 A1 | 9/2005 | Gertner et al. |
| 2005/0216042 A1 | 9/2005 | Gertner |
| 2005/0228504 A1 | 10/2005 | Demarais et al. |
| 2005/0240279 A1 | 10/2005 | Kagan et al. |
| 2005/0247320 A1 | 11/2005 | Stack et al. .................... 128/898 |
| 2005/0250980 A1 | 11/2005 | Swanstrom et al. |
| 2005/0251158 A1 | 11/2005 | Saadat et al. |
| 2005/0251162 A1 | 11/2005 | Rothe et al. |
| 2005/0256533 A1 | 11/2005 | Roth et al. |
| 2005/0256587 A1 | 11/2005 | Egan |
| 2005/0261712 A1 | 11/2005 | Balbierz et al. ................ 606/153 |
| 2005/0267405 A1 | 12/2005 | Shah |
| 2005/0267499 A1 | 12/2005 | Stack et al. |
| 2005/0267595 A1 | 12/2005 | Chen et al. |
| 2005/0267596 A1 | 12/2005 | Chen et al. |
| 2005/0273060 A1 | 12/2005 | Levy et al. |
| 2006/0015006 A1 | 1/2006 | Laurence et al. |
| 2006/0020278 A1 | 1/2006 | Burnett et al. |
| 2006/0058829 A1 | 3/2006 | Sampson et al. |
| 2006/0253142 A1 | 11/2006 | Bjerken |
| 2007/0027548 A1 | 2/2007 | Levine et al. |
| 2007/0060932 A1 | 3/2007 | Stack et al. |
| 2007/0276432 A1 | 11/2007 | Stack et al. .................... 606/213 |

FOREIGN PATENT DOCUMENTS

| | | |
|---|---|---|
| DE | 08708978 U1 | 11/1987 |
| DE | 8708978 U1 | 11/1987 |
| EP | 0775471 | 5/1997 |
| EP | 1492478 | 1/2005 |
| EP | 1602336 | 12/2005 |
| FR | 2768324 | 3/1999 |
| JP | 09-168597 | 6/1997 |
| WO | WO 91/01117 | 2/1991 |
| WO | WO 95/25468 A1 | 9/1995 |
| WO | WO 97/47231 | 12/1997 |
| WO | WO 00/12027 | 3/2000 |
| WO | WO 00/32137 | 6/2000 |
| WO | WO 00/78227 | 12/2000 |
| WO | WO 01/41671 | 6/2001 |
| WO | WO 01/45485 | 6/2001 |
| WO | WO 01/49359 | 7/2001 |
| WO | WO 01/66018 | 9/2001 |
| WO | WO 01/85034 | 11/2001 |
| WO | WO 01/89393 | 11/2001 |
| WO | WO 02/060328 | 8/2002 |
| WO | WO 03/017882 | 3/2003 |
| WO | WO 03/086246 | 10/2003 |
| WO | WO 03/086247 | 10/2003 |
| WO | WO 03/090633 | 11/2003 |
| WO | WO 03/094784 | 11/2003 |
| WO | WO 03/094785 A1 | 11/2003 |
| WO | WO 03/099137 | 12/2003 |
| WO | WO 2004/019765 A2 | 3/2004 |
| WO | WO 2004/019787 | 3/2004 |
| WO | WO 2004/032760 | 4/2004 |
| WO | WO 2004/037064 A2 | 5/2004 |
| WO | WO 2004/041133 | 5/2004 |
| WO | WO 2004/064680 | 8/2004 |
| WO | WO 2004/064685 | 8/2004 |
| WO | WO 2004/080336 | 9/2004 |
| WO | WO 2004/110285 | 12/2004 |
| WO | WO 2005/037152 | 4/2005 |
| WO | WO 2005/079673 | 9/2005 |
| WO | WO 2005/096991 | 10/2005 |
| WO | WO 2005/105003 | 11/2005 |
| WO | WO 2006/016894 | 2/2006 |
| WO | WO 2006/055365 | 5/2006 |
| WO | WO 2006/127593 | 11/2006 |
| WO | WO 2009/011882 A2 | 1/2009 |

OTHER PUBLICATIONS

International Search report and Written Opinion for PCT application PCT/US2004/033007, Feb. 9, 2005, 12 pages (2005).

International Search Report from PCT Patent Application No. PCT/US2002/027177 mailed Feb. 14, 2003.
International Search Report from PCT Patent Application No. PCT/US2003/004378 mailed Aug. 13, 2003.
International Search Report from PCT Patent Application No. PCT/US2003/033605 mailed Mar. 29, 2004.
International Search Report from PCT Patent Application No. PCT/US2003/033606 mailed Mar. 29, 2004.
International Search Report from PCT Patent Application No. PCT/US2003/004449 mailed Aug. 13, 2003.
International Search Report from PCT Patent Application No. PCT/US2004/006695 mailed Sep. 8, 2004.
International Search Report from PCT Patent Application No. PCT/US2005/014372 mailed Jul. 28, 2005.
International Search Report from PCT Patent Application No. PCT/US2006/019727 mailed Apr. 19, 2007.
International Search Report from PCT Patent Application No. PCT/US2006/038684 mailed Feb. 14, 2007.
International Search Report from PCT Patent Application No. PCT/US2007/019227 mailed Feb. 20, 2008.
Stecco, et al., "Trans-oral plication formation and gastric implant placement in a canine model", Stecco Group, San Jose and Barosense, Inc., Redwood City, CA (2004).
Stecco, et al. "Safety of a gastric restrictive implant in a canine model", Stecco group, San Jose amd Barosense, Inc., Redwood City, CA (2004).

* cited by examiner

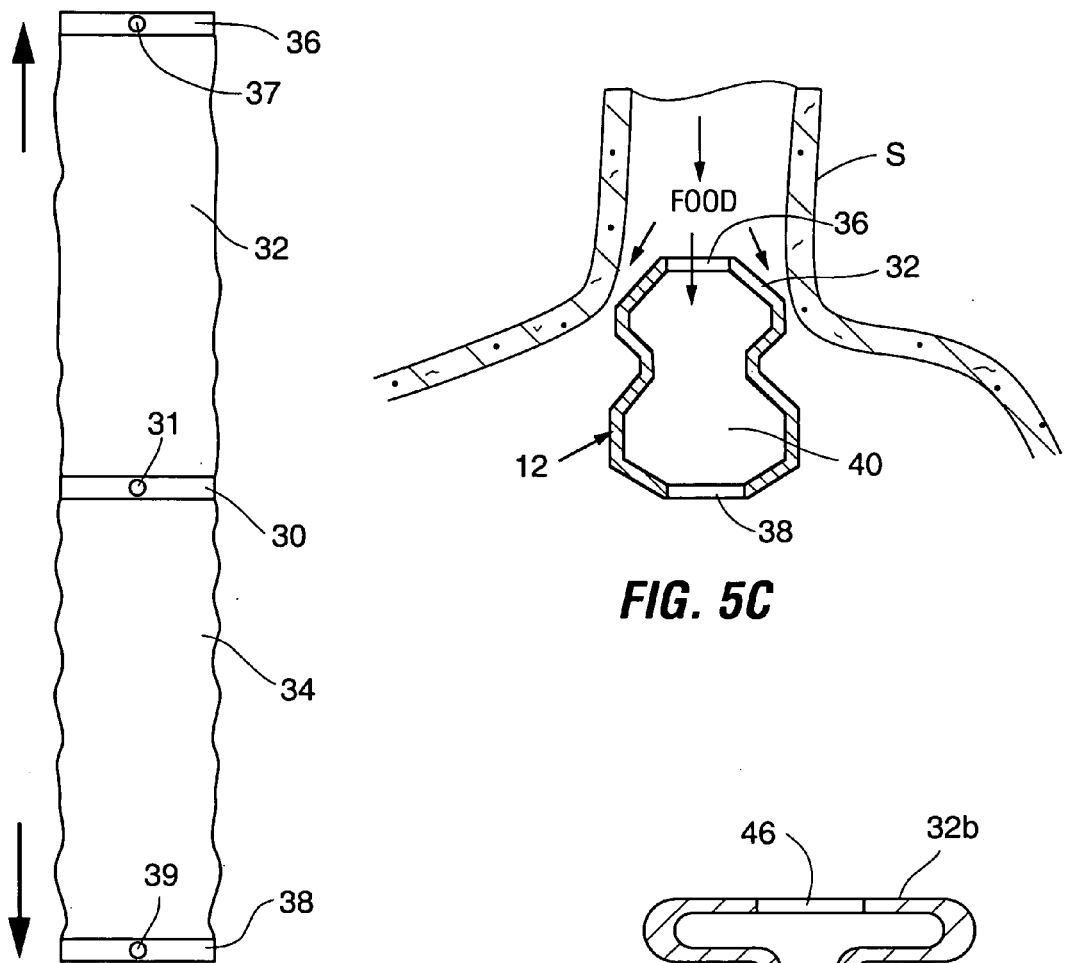
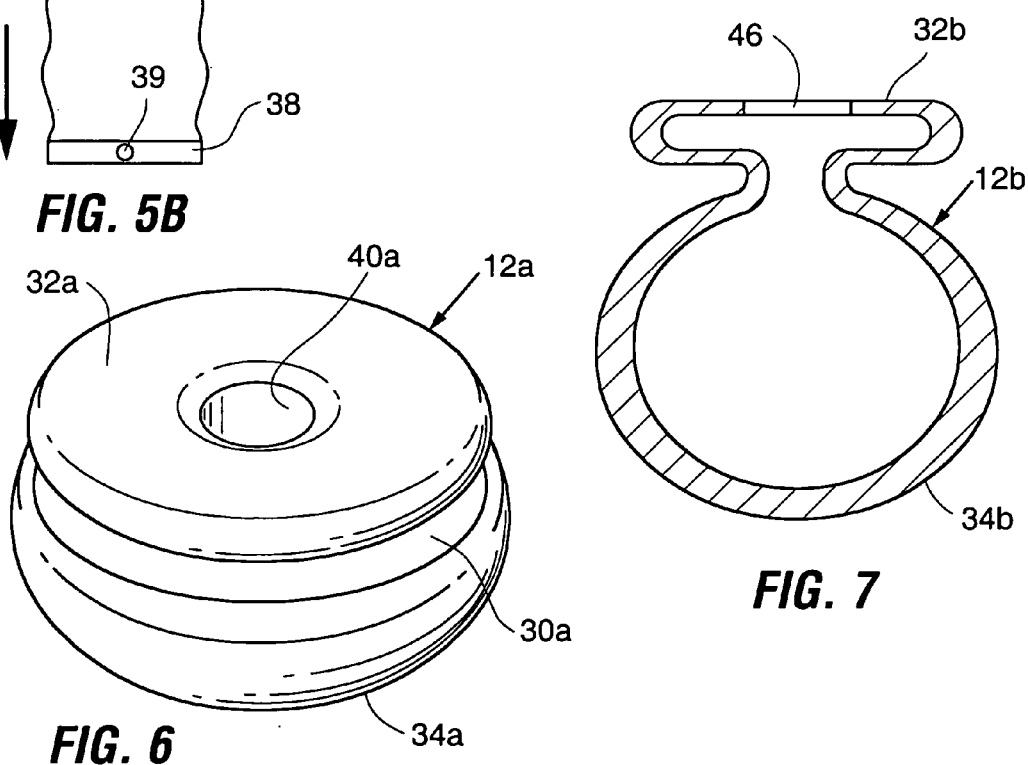

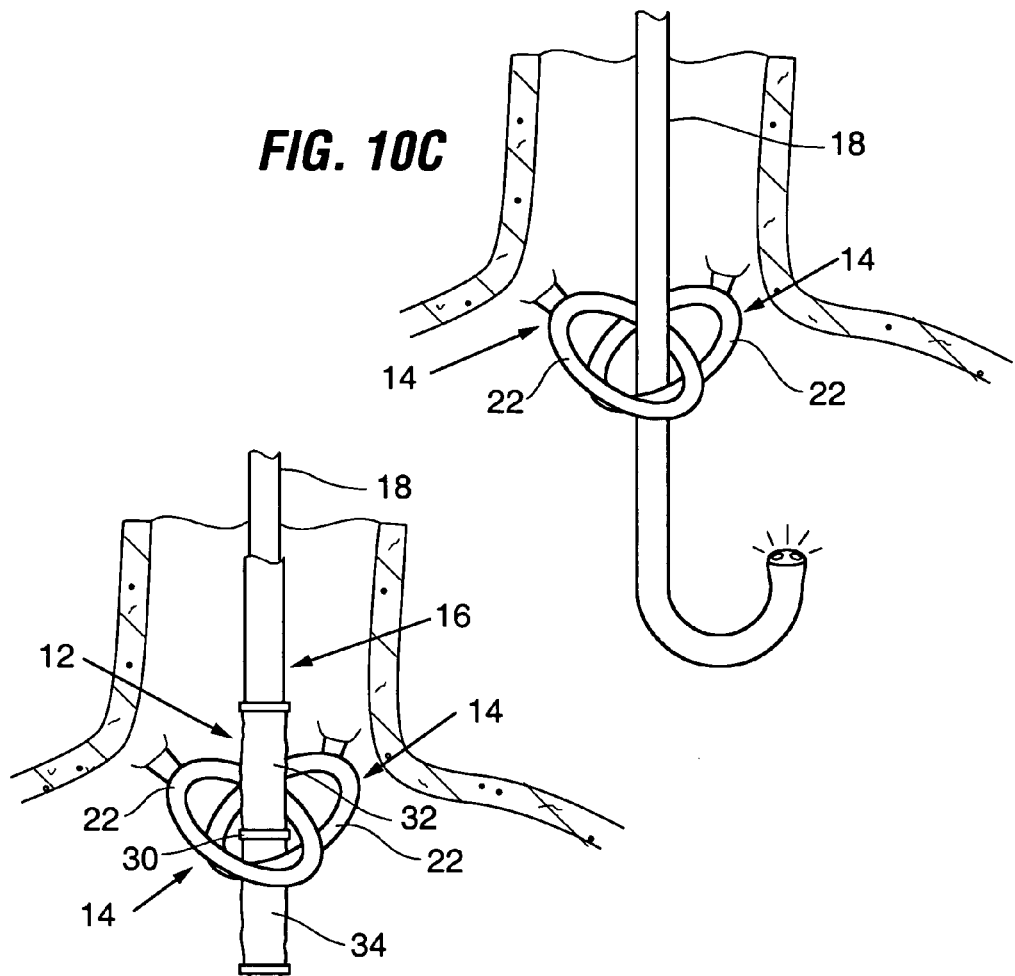
FIG. 10C
FIG. 10D
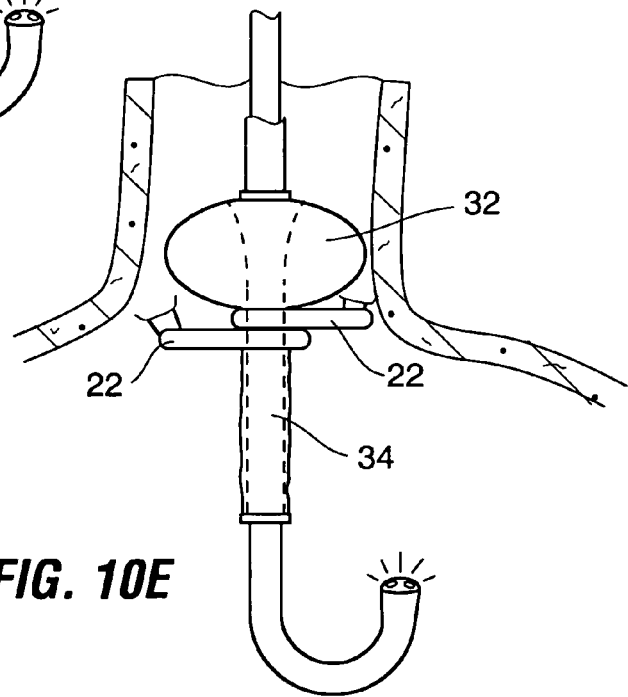
FIG. 10E ing a method for forming a tissue tunnel of the type shown in
RESTRICTIVE AND/OR OBSTRUCTIVE IMPLANT SYSTEM FOR INDUCING WEIGHT LOSS

PRIORITY

The present application claims the benefit of U.S. Provisional Application No. 60/683,635, filed May 23, 2005 and is a continuation-in-part of U.S. patent application Ser. No. 10/575,222, filed Jul. 30, 2007 which is a continuation of PCT/US2004/033007, filed Oct. 8, 2004, which is a continuation-in-part of U.S. patent application Ser. No. 10/843,702, filed May 11, 2004, which claims the benefit of U.S. Provisional Application No. 60/510,268, filed Oct. 10, 2003 and a continuation-in-part of U.S. patent application Ser. No. 10/898,036, filed Jul. 23, 2004, now U.S. Pat. No. 7,431,725, which claims the benefit of U.S. Provisional Application No. 60/510,268, filed Oct. 10, 2003.

FIELD OF THE INVENTION

The present invention relates generally to the field of implants for inducing weight loss in patients, and specifically to devices and methods for reducing the effective volume of a patient's stomach and/or creating restrictions to slow passage of food into the stomach.

BACKGROUND OF THE INVENTION

An anatomical view of a human stomach S and associated features is shown in FIG. 1A. The esophagus E delivers food from the mouth to the proximal portion of the stomach S. The z-line or gastro-esophageal junction Z is the irregularly-shaped border between the thin tissue of the esophagus and the thicker tissue of the stomach wall. The gastro-esophageal junction region G is the region encompassing the distal portion of the esophagus E, the z-line, and the proximal portion of the stomach S.

Stomach S includes a fundus F at its proximal end and an antrum A at its distal end. Antrum A feeds into the pylorus P which attaches to the duodenum D, the proximal region of the small intestine. Within the pylorus P is a sphincter that prevents backflow of food from the duodenum D into the stomach. The middle region of the small intestine, positioned distally of the duodenum D, is the jejunum J.

FIG. 1B illustrates the tissue layers forming the stomach wall. The outermost layer is the serosal layer or "serosa" S and the innermost layer, lining the stomach interior, is the mucosal layer or "mucosa" MUC. The submucosa SM and the multi-layer muscularis M lie between the mucosa and the serosa.

Prior art treatments for obesity range from diet and medication to highly invasive surgical procedures. Some of the more successful surgical procedures are the vertical banded gastroplexy or the proximal gastric pouch with a Roux-en-Y anastomosis. However, known complications are present with each of these procedures. More successful and less invasive options are desired.

BRIEF DESCRIPTION OF THE DRAWINGS

FIG. 5B is a side elevation view of the implant of FIG. 5A in the streamlined implantation position.

FIG. 5C is a cross-sectional side elevation view of an implant positioned within a stomach.

FIG. 6 is a perspective view of an alternative embodiment of an implant.

FIG. 7 is a cross-sectional side elevation view of a second alternative embodiment of an implant.

FIGS. 10A through 10F are a sequence of drawings illustrating use of the system of FIG. 2 to position an implant.

DETAILED DESCRIPTION

Figure 1A:
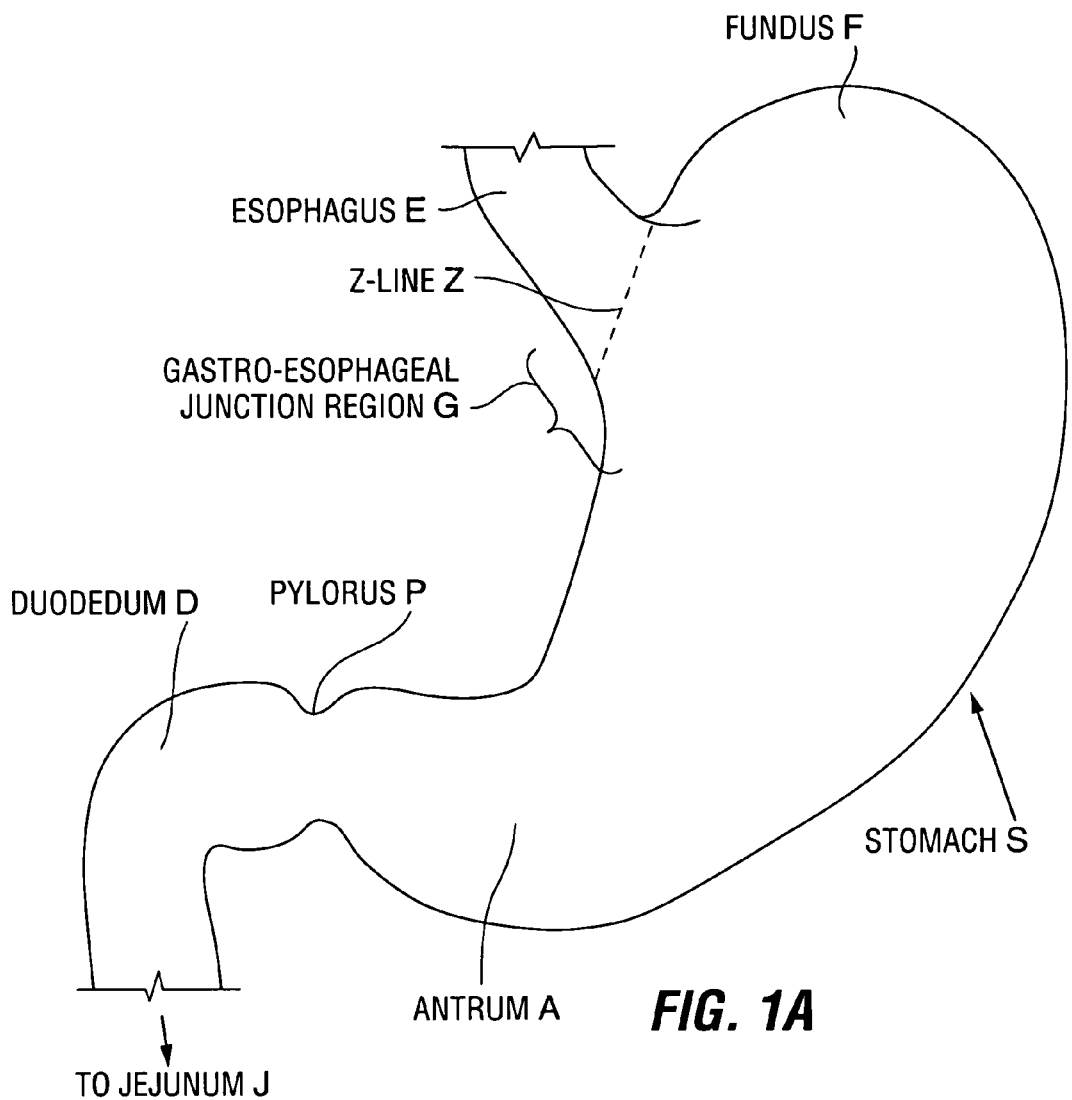
FIG. 1A is a schematic illustration of a human stomach and a portion of the small intestine.

The drawings show a number of implants intended to induce weight loss in one or more of a variety of ways, as well as anchoring devices that support such implants within the stomach.

For the purposes of this application, the terms "restrictive devices", "satiation devices," or "obstructive devices" will be used to mean implants intended to induce weight loss in one or more of a variety of ways. These include, but are not limited to, slowing the rate at which food passes from the esophagus into the stomach, physically restricting the amount of food that can be consumed, effectively reducing the stomach volume, and/or imparting pressure against portions of the GI system (e.g. stomach, esophagus, esophageal sphincter, etc) causing the patient to experience sensations of fullness, and/or affecting levels of hormones or other substances in the body that control or affect feelings of hunger, and/or affecting the amount of ingested food absorbed by the body. The anchoring devices and methods described herein are useful for various types of satiation implants, including those not specifically described herein and including those positionable in the esophagus, the gastro-esophageal junction region and other portions of the stomach including the proximal stomach, fundus, antrum, etc.

The devices may be provided in one or more kits, which may further comprise instructions for use according to any of the implantation and/or retention methods described herein. Optionally, such kits may further include any of the other system components described in relation to the devices and associated methods, and any other materials or items relevant to those devices and methods. For example, kits may include endoscopic or laparoscopic stapling, suturing and/or cutting instruments, guidewires, positioning mandrels, and any other tools needed to carry out the procedure.

It should be noted that although the embodiments are described in the context of satiation devices, certain of the described components and methods might be equally suitable with other types of implants. These implants include, but are not limited to prosthetic valves for the treatment of gastro-esophageal reflux disease, gastric stimulators, pH monitors and drug eluting devices that release drugs, biologics or cells into the stomach or elsewhere in the GI tract. Such drug eluting devices might include those which release leptin (a hormone which creates feelings of satiety), Ghrelin (a hormone which creates feelings of hunger), octreotide (which reduces Ghrelin levels and thus reduces hunger), Insulin, chemotherapeutic agents, natural biologics (e.g. growth factor, cytokines) which aid in post surgery trauma, ulcers, lacerations etc. As yet another example, the implant may provide a platform to which specific cell types can adhere, grow and provide biologically-active gene products to the GI tract. As other alternatives, an implant may provide a platform for radiation sources that can provide a local source of radiation for therapeutic purposes, or provide a platform whereby diagnostic ligands are immobilized and used to sample the GI tract for evidence of specific normal or pathological conditions, or provide an anchor point for imaging the GI tract via cameras and other image collecting devices.

It should also be noted that certain embodiments described herein have applicability for retaining implants in parts of the body outside the GI system. Thus, the term "implant" will thus be used to refer to satiation devices as well as other types of medical devices that may be implanted in the esophagus, gastro-esophageal junction, stomach, elsewhere within the GI tract, or in other hollow organs, vessels, and cavities of the body.

Figure 2:
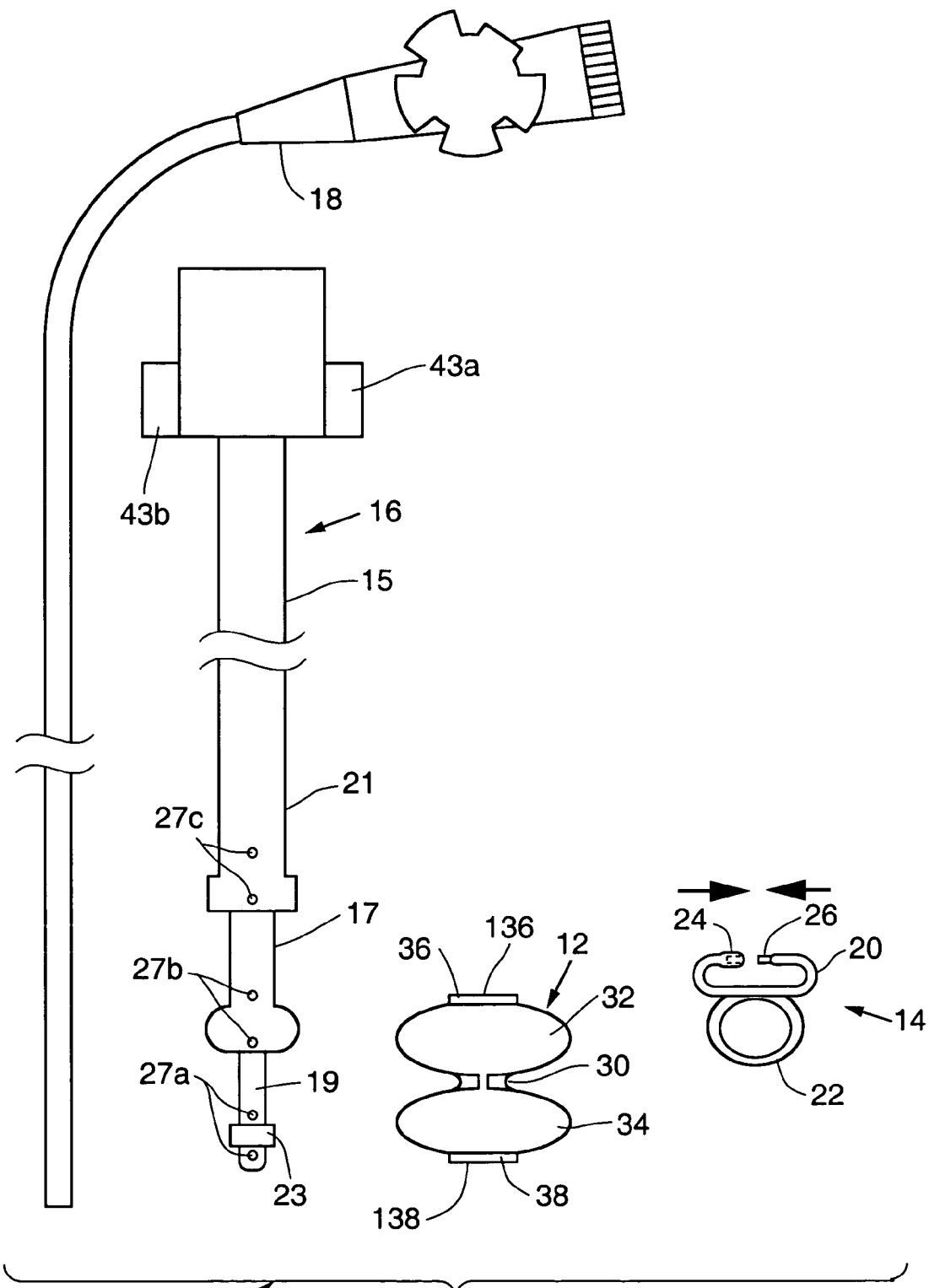
FIG. 2 is a side elevation view of one embodiment of an implant system, including an endoscope, delivery tool, implant, and anchor.

FIG. 2 shows one embodiment of an implant system 10 for inducing weight loss. System 10 includes a satiation implant 12, and one or more anchors 14 for supporting the implant within a stomach, such as in the region of the gastro-esophageal junction, and a delivery tool 16 for use in introducing and positioning the implant 12. System 10 may optionally include an endoscope 18, which may be one of various endoscopes available for use in endoscopic procedures.

Figure 3A:
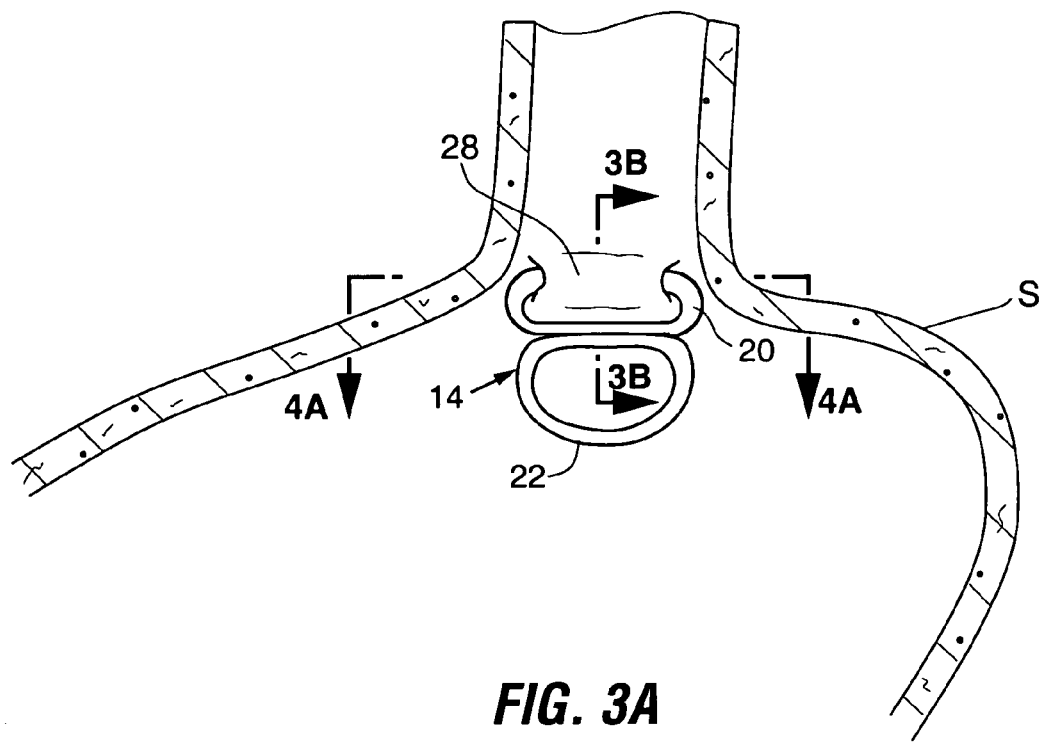
FIG. 3A is a schematic illustration of a human stomach illustrating a tissue tunnel formed at the gastro-esophageal junction region of a stomach.

Anchor 14 includes a fastener 20 and a loop 22. Fastener 20 serves as a coupling device that enables the anchor to be coupled to a tissue structure within the stomach. It is preferably a C-bar type fastener and includes male and female connectors 24, 26 that engage with one another as indicated by arrows in FIG. 2. Referring to FIG. 3A, fastener 20 is proportioned to be suspended from a tissue tunnel 28 formed using stomach wall tissue as will be discussed in more detail in connection with FIGS. 8A through 8F. During implantation of the anchor, one connector 24 of fastener 20 is preferably threaded through the tissue tunnel 28 and engaged with the other connector 26 to form the fastener into a loop encircling a portion of the tissue tunnel. This is advantageous in that the anchor 14 may be coupled to the tissue without penetration of the mucosal tissue by the anchor 14 or associated sutures, staples, etc, although such penetration may be used if desired. Anchor 14 may be formed of a flexible material that will withstand the acidic environment of the stomach. Examples of such materials include, but are not limited to polyesters (e.g. Dacron® polyester), ePTFE fabric (e.g. GoreTex® fabric or others), a urethanes such as ChronoFlex® polyurethane, nylon fabrics, silicone, other polymeric materials.

Figure 4A:
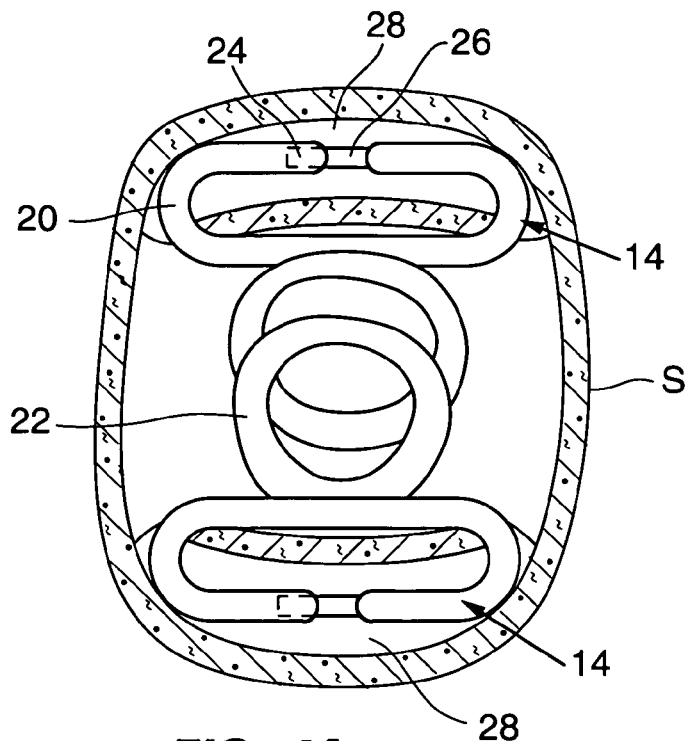
FIG. 4A is a cross-section view of a stomach taken along the plane designated 4A-4A in FIG. 3A and further illustrating retention of two anchors of the type shown in FIG. 2 within the tissue tunnels.
Figure 4B:
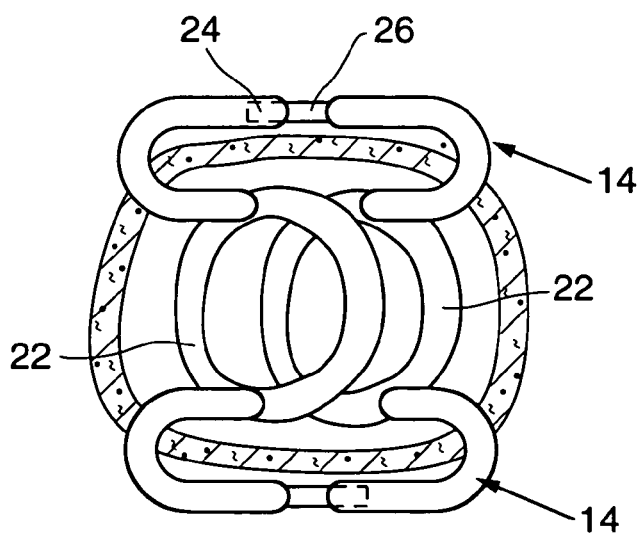
FIG. 4B is a cross-section view similar to FIG. 4A showing an alternative arrangement of two anchors of the type shown in FIG. 2 within the tissue tunnels.
Figure 4C:
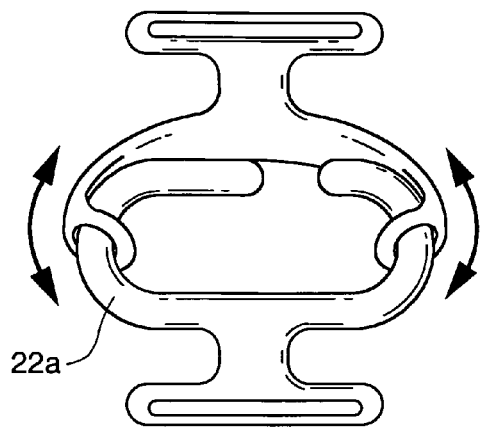
FIG. 4C is a perspective view of an alternative embodiment of an anchor.

The anchor 14 may be used alone or in combination with one or more additional anchors. As illustrated in FIG. 4A, in a first embodiment two or more of such anchors 14 are positioned in separate tissue tunnels 28, with the loops 22 of the anchors 14 roughly aligned with one other. This arrangement allows the anchors to be independent of one another so as to minimize tensile forces between the anchors in response to movement of the stomach walls. Alternatively, the anchors may be interconnected. For example in the arrangement shown in FIG. 4B, the anchors are positioned with the male connector 24 of each anchor coupled to the female connector 26 of the other anchor. In a variation of this embodiment, a single anchor may be used in which a single loop (similar to loop 22) is provided with two or more fasteners 20 connected to it. In either of these latter embodiments, an element of play can be built into the loop so as to minimize tensile forces between the fasteners. For example, as shown in FIG. 4C, the loop 22a may be formed of mating components that slide relative to one another in response to movement of the stomach walls.

Figure 4D:
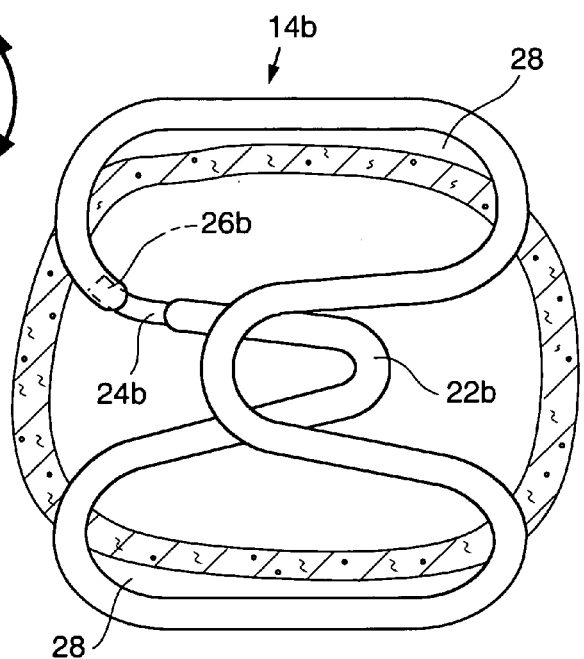
FIG. 4D is a cross-section view similar to FIG. 4A showing a second alternative embodiment of an anchor.

FIG. 4D illustrates yet another alternative anchor 14b in which the anchor 14b is formed of a flexible elongate band having mating elements such as connectors 24b, 26b. This anchor 14b may be implanted by feeding one end of the band through two or more tissue tunnels 28 in a manner which forms a portion of the band into a loop 22b as shown. The sections of the band forming the loop may lie on top of one another as shown in FIG. 4D, or they may be intertwined.

Referring again to FIG. 2, implant 12 is proportioned to be securely held within the loop 22 of the anchor 14. In one embodiment, implant 12 includes a relatively narrow waist section 30 situated between an orad section 32 and an aborad section 34. With this arrangement, the loop 22 of anchor 14 can engage the waist section 30 as described with respect to FIGS. 10E-10F so as to support the implant 12 within the stomach.

Figure 5A:
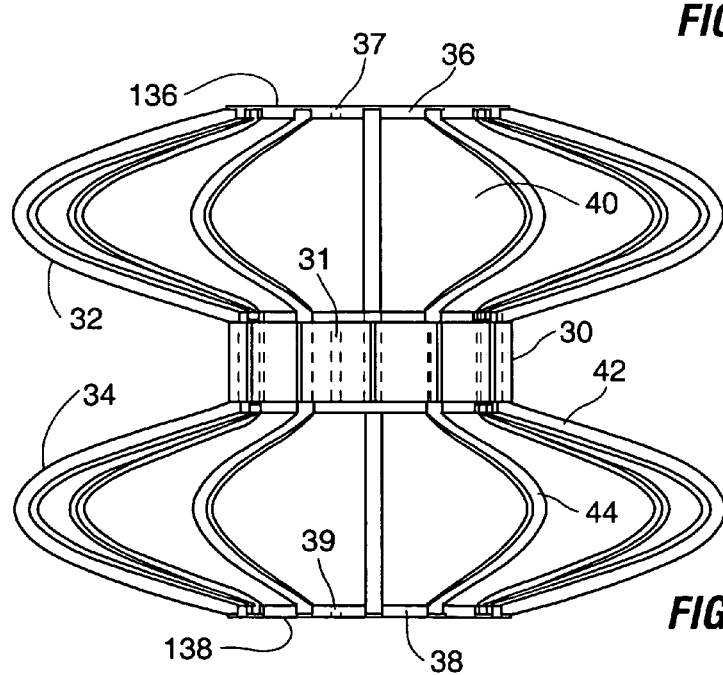
FIG. 5A is a side elevation view of an implant in the radially expanded position.

Referring to FIGS. 2 and 5A, implant 12 preferably includes a an orad ring 36 surrounding an orad opening 136 and an aborad opening 138 surrounded by ring 38. The waist section 30 may include a ring similar to rings 36, 38.

A passageway 40 ends between the openings 136, 138. Passageway 40 allows for access by an endoscope and other instruments as detailed in the Implantation section below. The implant 12 may be hollow, in which case the passageway 40 may be continuous with the hollow interior of the implant. Alternatively, the implant may be toroidal, with the passageway forming the central opening of the toroid (see FIG. 6).

Implant is preferably made of a flexible, self expandable, material suitable for use within the stomach. Examples include polyesters (e.g. Dacron® polyester), ePTFE fabric (e.g. GoreTex® fabric or others), urethanes such as ChronoFlex® polyurethane, nylon fabrics, silicone, latex, or other polymeric materials. As shown in FIG. 5A, implant 12 may include a frame 42 (e.g. which may be formed of a mesh, strut elements 44 and/or other features). The frame is preferably manufactured using nitinol or shape memory polymers to facilitate self-expansion of the implant. Frame 42 may be provided with a covering or coating formed of Dacron® polyester, silicone, urethanes or other material, or it may be provided without a covering or coating. The implant materials are sufficiently flexible to allow the implant 12 to be manipulated to a streamlined position, such as by applying tension between the orad section 32 and the aboard section 34 as shown in FIG. 5B, or by compressing the implant radially inwardly. The waist 30 and the rings 36, 38 and may include small holes 31, 37 and 39, respectively, for receiving wires, sutures, or other elements that may be used to anchor the implant 12 on an implantation tool.

The shape and dimensions of the implant 12 are selected to induce weight loss by restricting patient eating in one or more ways. For example, referring to FIG. 5C, the implant 12 may be contoured such that when the orad section 32 is positioned in close proximity to the surrounding walls of the gastro-esophageal junction region, very little food can pass around the implant 12, and the dimensions of the passageway 40 restrict the amount of food that can pass through the passageway 40 at one time. Thus, the restrictive and obstructive nature of the device slows passage of food from the esophagus into the stomach, and prevents the patient from eating large quantities of food. In various embodiments, the dimensions of the passageway 40 may be selected based on the amount of flow restriction needed for the patient. In other embodiments, the passageway 40 may be sealed, extremely narrow, or absent from the implant so as to cause all ingested food to eventually flow around the limited space around the perimeter of the implant.

The implant preferably includes soft, atraumatic edges in regions that might contact the surface of stomach mucosa, to prevent irritation of the tissue. In one alternative embodiment, the outer profile of the implant may be spherical or semi-spherical such that the device can roll over the stomach surface during movement of the stomach.

In an alternative implant 12a shown in FIG. 6, the surface of orad section 32a is substantially flat. The aboard section 34a may be curved as shown, or it may be flat.

FIG. 7 shows an alternative embodiment of an implant 12b which functions as a space occupier in addition to or as an alternative to restricting flow of food from the esophagus to the stomach. In the FIG. 7 embodiment, the aboard section 34b is sufficiently large to occupy sufficient space within the stomach to create feelings of satiety and/or to reduce stomach capacity. In some embodiments, the implant 12b may have an expanded volume in the range of approximately 200-700 cc, sufficient to fill a portion of the stomach, thereby causing the patient to feel full and thus limiting food intake. Implant 12b may be inflatable, and it may include an inflation port 46 or a region of self-sealing material, either of which may be engaged by an inflation tube introduced into the stomach after the implant is positioned.

Figure 1B:
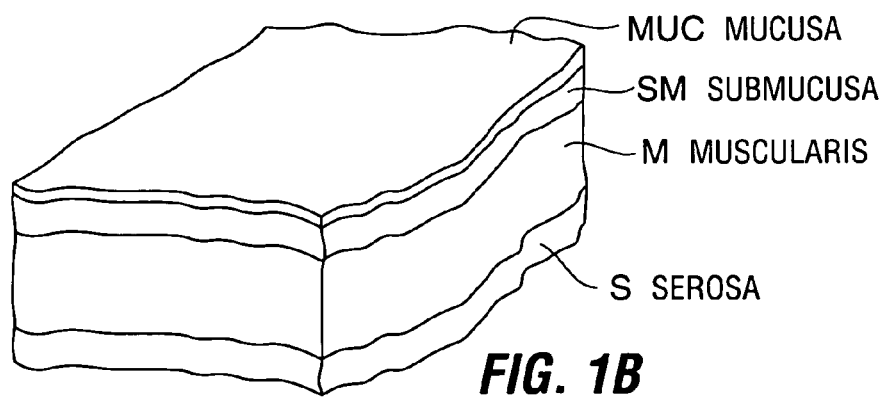
FIG. 1B is a cross-sectional perspective view of a portion of a stomach wall, illustrating the layers of tissue forming the wall.

The FIG. 7 embodiment may be positioned at various locations within the stomach. For example, it may be positioned in the gastro-esophageal junction region or the fundus where it may function to occupy space so as to reduce effective stomach volume, but also to create restrict the rate at which food can descend from the esophagus into the stomach as discussed with prior embodiments. Alternatively, it may be positioned in the antrum A or the pylorus P (FIG. 1 A) to reduce the effective stomach volume and/or to slow the exit of food from the stomach into the intestines.

Referring again to FIG. 2, implantation tool 16 for the implant 12 of FIG. 2 includes an outer shaft 15, a middle shaft 17 and an inner shaft 19. Outer shaft 15 is arranged to receive the orad section 32 of the implant and may include a broadened mount 21 to facilitate seating of the orad ring 36 on the shaft 15. Similarly, inner shaft may also have a mount 23 for receiving the aboard section 34 of the implant 12, and middle shaft 17 might also include a mount 25 for accommodating the waist section 30 of the implant 12. Shafts 15, 17, 19 are slidable telescopically relative to one another. Thus, the shafts may be moved to an expanded position to spread the mounts 21, 23, 25 relative to one another and to thus elongate the implant into the streamlined orientation shown in FIG. 5B. Similarly, the shafts may be adjusted to close the spacing between the mounts 21, 23, 25, thereby allowing the implant to assume its natural orientation.

Retraction of the shafts may be actuated using release tabs 43a, 43b on the handle of the implantation tool. For example, the implantation tool 16 may include spring loaded latches (not shown) that retain the tool in the expanded position and that are disengaged using the release tabs 43a, 43b. Thus, for example, depression of release tab 43a will release the latch associated with outer shaft 15, thus causing the outer shaft to slide distally relative to the middle shaft 17. Similarly, actuation of release tab 43b will disengage the latch associated with inner shaft 19 so as to allow the inner shaft to slide proximally relative to the middle shaft. In this embodiment, movement of the shafts upon release of the latches may be spring biased or manual.

Small holes 27a, b, c may be formed in each of the shafts 15, 17, 19 for receiving wires, sutures, or other elements that may be used to anchor the implant 12 on the implantation tool 16.

Alternative implantation tools may rely on other mechanisms for delivering the implant to the desired location. For example, alternative tools may include retractable elements for grasping portions of the implant (e.g. the rings or loops such as the loops 84, 86 shown in FIG. 11A) and then releasing the implant when it is the proper position. Alternative embodiments may also rely solely on the shape memory properties of the implant for expansion of the implant within the body.

Anchor Implantation

Exemplary methods for implanting anchors 14 will next be described.

In a preferred method, tissue tunnels 28/28a (FIGS. 3A-3C) are formed to provide an anatomical structure on the stomach wall to which the anchors 14 may be coupled. The tunnels may be formed using laparoscopic, endoscopic, and/or surgical approaches. Various procedures for forming tissue s/tunnels are described in Applicant's prior application WO 2005/037152, entitled "Devices and Methods for Retaining a Gastro-Esophageal Implant" published Apr. 25, 2002, which is commonly owned with the present application and which is incorporated herein by reference.

As discussed in the prior application, tissue tunnels may be created using tissue plications formed by grasping sections of tissue and stapling or suturing the tissue together to form tissue structures. Such structures may be tunnel-like in the sense that they have an interior space bounded by tissue, and openings positioned so that an anchor or other portion of a medical device may be passed through one opening, through the interior space of the tunnel, and out the other opening. The interior walls of the tunnel may lie in contact with one another, collapsing the interior space in the same way the space within a shirt is collapsed. In other embodiments, the tunnels may retain a more tubular shape.

Several such procedures rely in part on adhesion of the serosal tissue lining the outer surface of the stomach. It has been found that serosal tissue layers can adhere to form relatively strong bonds when held in apposition to one another.

Figure 3B:
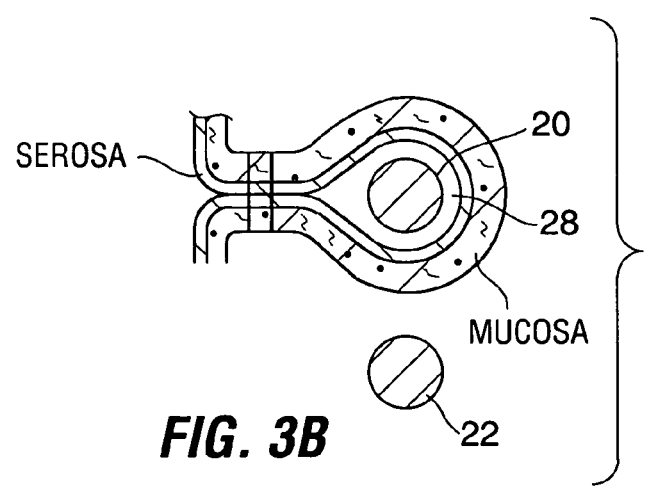
FIG. 3B is a cross-section view of the tissue tunnel of FIG. 3A, taken along the plane designated 3B-3B.
Figure 3C:
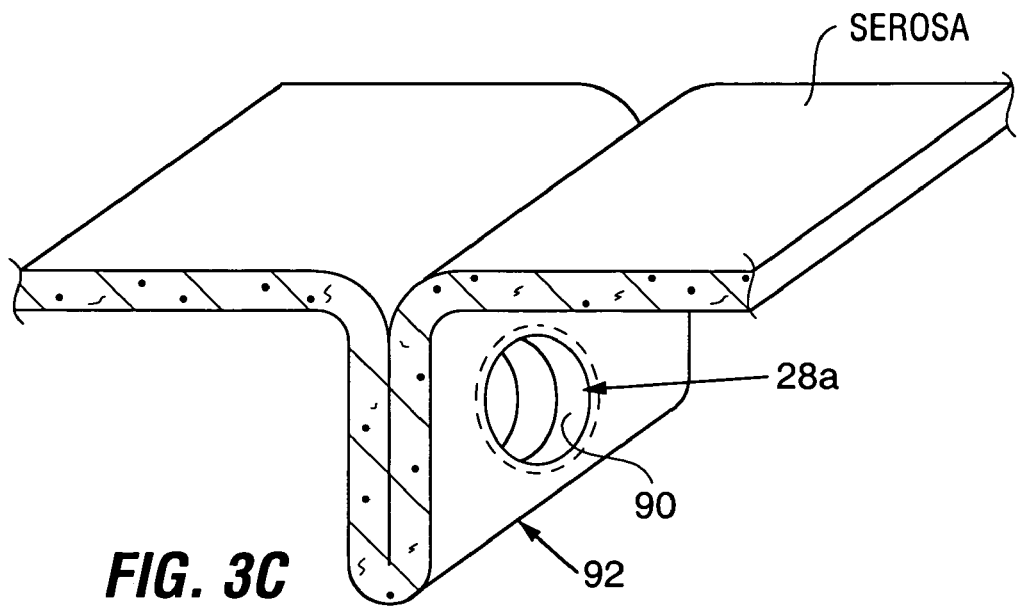
FIG. 3C is a cross-sectional perspective view of a portion of stomach wall, showing another type of tissue tunnel that may be used.
Figure 3D:
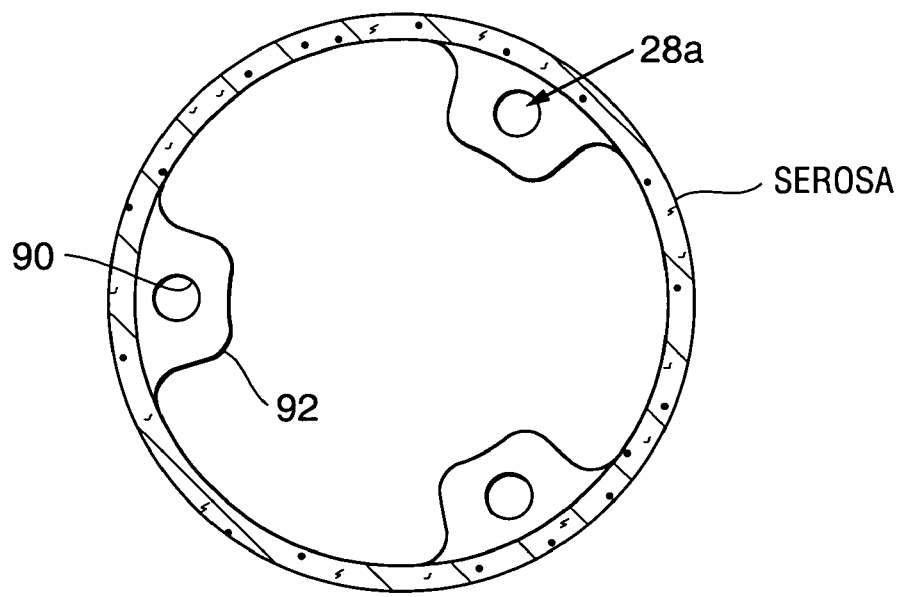
FIG. 3D is a cross-sectional top view of a stomach showing three such tissue tunnels in tissue plications formed on the wall of a stomach.

For example, the tissue tunnels might be similar to the tunnels 28 shown in FIGS. 3A and 3B, or they might alternately be tunnels 28a of the type shown in FIGS. 3C and 3D created by forming holes 90 in serosal tissue plications 92. Methods for forming either type of tissue tunnel may be carried out in a manner that takes advantage of the strong adhesions formed when serosal tissue surfaces are held in apposition. Other methods not specifically described herein may also be used without departing from the scope of the present invention.

FIGS. 8A through 8F illustrate one method of forming tissue tunnels (also referred to as tissue pockets) such as the type shown in FIGS. 3A and 3B.

The orientation of the tunnels is chosen to best accommodate the particular type of anchor/implant arrangement to be used. For example, tunnels may have an orad-aboral orientation as shown in FIG. 8F, or a more transverse orientation as in FIGS. 3A and 4A.

Figure 8A:
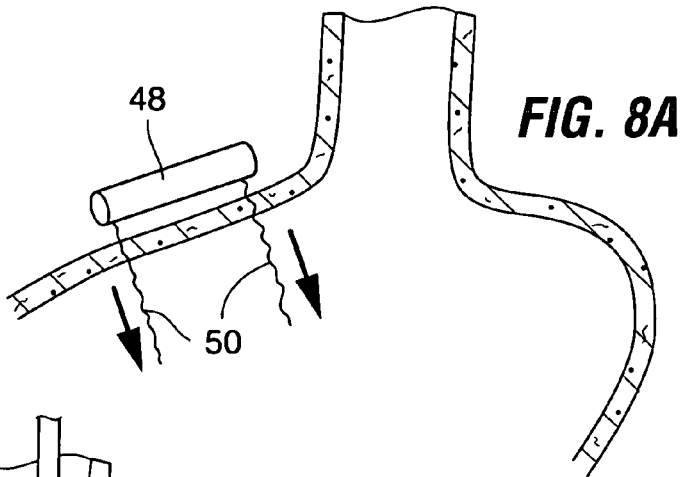
FIGS. 8A through 8F are a sequence of drawings illustrating a method for forming a tissue tunnel of the type shown in FIG. 3A on the wall of a stomach.
Figure 8B:
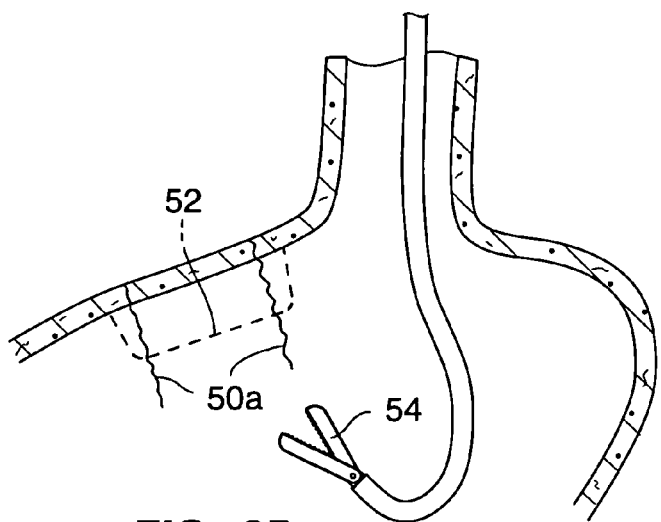

Referring to FIG. 8A, a rod 48 is positioned on the exterior surface of the stomach, and sutures 50 are attached to the rod 48 and passed through the stomach walls. The sutures 50 are drawn inwardly using an endoscopic grasper (not shown) to "tent" a section 52 of tissue of the type shown in FIG. 8C. If desired, the method may be performed without the rod 48 as shown in FIG. 8B, in which case a pair of sutures 50a may be passed from the stomach interior, through the stomach wall, and then back into the stomach interior, and then drawn inwardly using an endoscopic grasper 54 to tent the tissue as shown in dashed lines.

Figure 8C:
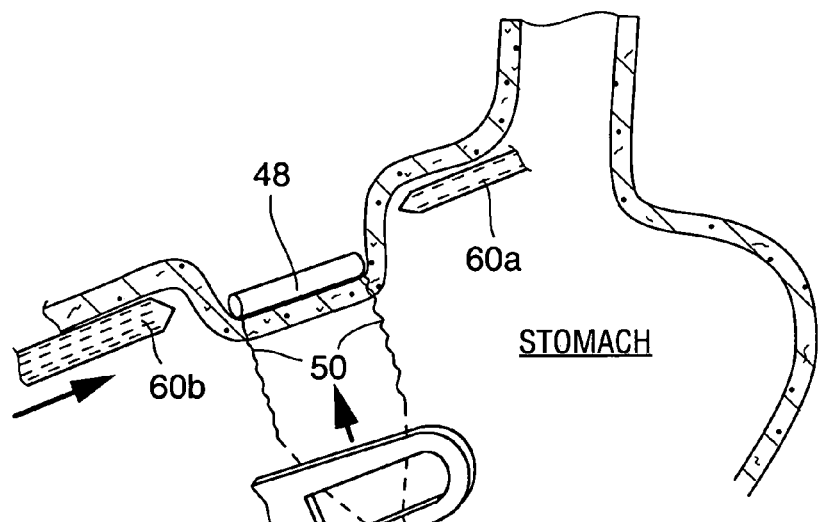
Figure 8D:
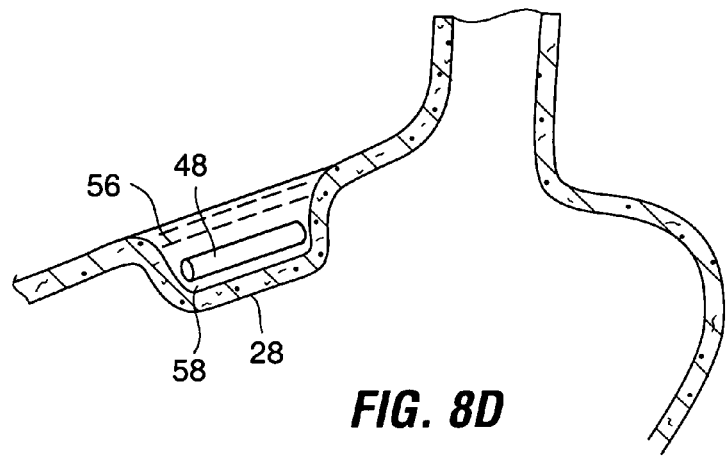

Next, a line 56 of staples or sutures are applied across the tented tissue from the mucosal side of the stomach—thereby forming an enclosed pocket 58 on the exterior surface of the stomach as shown in FIG. 8D. The rod 48 (if used) is enclosed within the pocket 58. Stapling/suturing may be performed using an endoscopic stapler 60a passed through the esophagus into the stomach, or using a laparoscopic stapler 60b introduced into the stomach through a surgical gastronomy site—both of which are shown in FIG. 8C. The stapler/suture device preferably has characteristics that will form a suture/staple line 56 that is sufficiently patent to seal the serosal tissue together to prevent stomach leakage prior to complete serosal adhesion, but that ensures good blood flow so as to promote healing of the stapled tissue. For example, a conventional stapler modified to have a staple cartridge in which alternate staples have been removed may achieve this purpose.

A collar 62 may be placed around the tented tissue 52 as shown in FIG. 8C prior to suturing/stapling so as to apply tension to the wall tissue to facilitate suturing or stapling.

Figure 8E:
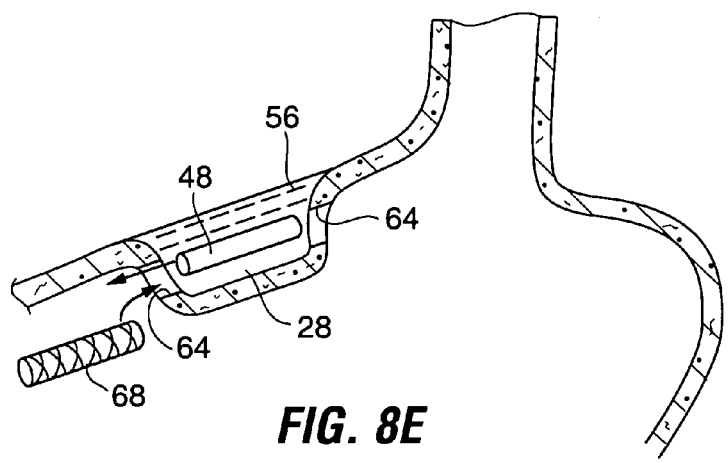
Figure 8F:
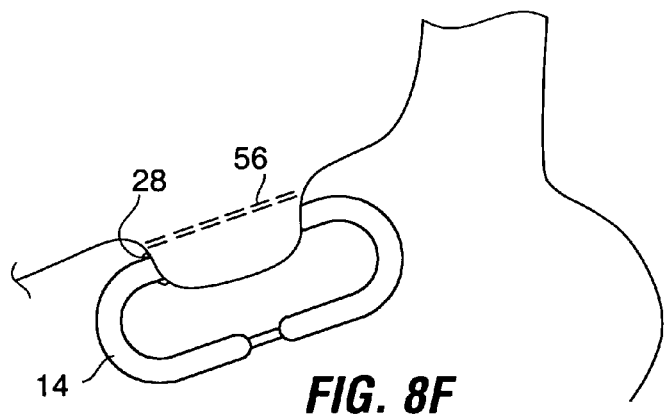

The suture line 56 holds the serosal layers of tissue together as shown in FIG. 8E, thereby holding the pocket 58 together. The ends 64 of the pocket are cut, turning the enclosed pocket 58 into a tissue pocket or tunnel 28 having ends that open into the stomach interior. The rod 48, if used, is removed from the tunnel 28. The tissue preferably heals together to form an adhesion that maintains the tunnel.

Because the tissue tunnel 28 is formed of serosal tissue, it may be desirable to line the tunnel/28 with a stent-like device 68 or another liner to both reinforce the and protect the serosal surface from the acidic stomach environment. Many of the embodiments described above rely upon formation of tissue adhesions between opposed tissue layers. The liner may also function as scaffolding that promotes tissue ingrowth and/or function to reinforce the adhesions that form.

The procedure is repeated to form as many tunnels as are needed to support the desired number of anchor(s) in the stomach. Over time, the regions of tissue held in apposition will adhere together due to the body's physiological or biological response, such as formation of fibrous tissue or scar tissue, growth of new tissue, or a growing, healing, or knitting together of the opposed tissue layers. The term "adhesion" will be used in this application to refer to the adhering of opposed tissue layers as a result of any physiological or biological response, including but not limited to those listed above.

To form tissue tunnels 28a of the type shown in FIGS. 3C and 3D, a serosal plication 92 is formed. More specifically, tissue within the stomach interior is pinched together to draw serosal layers on the stomach exterior into contact with one another, thereby forming a folded tissue tab or plication 92. A hole 90 is formed in the plication 92 and staples 94 or sutures, etc., are placed around the hole 90 to keep the tissue pinched together until a serosal adhesion forms. Multiple plications 92 may be formed as shown in FIG. 3D.

Once the tunnels 28 (or 28a) are formed, one or more anchor(s) 14 may be coupled to the tunnels. In a preferred method, the tunnels are allowed to heal and then a later procedure is carried out to couple the anchors 14 to the tunnels and to position the implant 12. If desired, however, the anchors may be implanted during the same procedure in which the tunnels are formed, and the implant may then be positioned in a later procedure after the tunnels have healed. Naturally, tunnel formation, anchor attachment, and implant positioning may also be performed in three separate procedures.

To implant the anchors 14, each anchor is passed through the esophagus and into the stomach, preferably under endoscopic visualization. The anchor 14 and associated instruments may be passed down a sheath positioned in the esophagus so as to protect the surrounding tissues. A portion of the fastener 20 of the anchor is passed through the tissue tunnel 28, and the connectors 24, 26 are engaged to form the fastener 20 into a loop as shown in FIG. 4A. An endoscopic grasper or other suitable endoscopic instruments may be used for this purpose. According to the first embodiment, a second anchor is coupled to a second tissue tunnel as shown. At this point, the loops 22 of the anchors 14 preferably overlap and are ready to receive the implant 12.

Figure 9A:
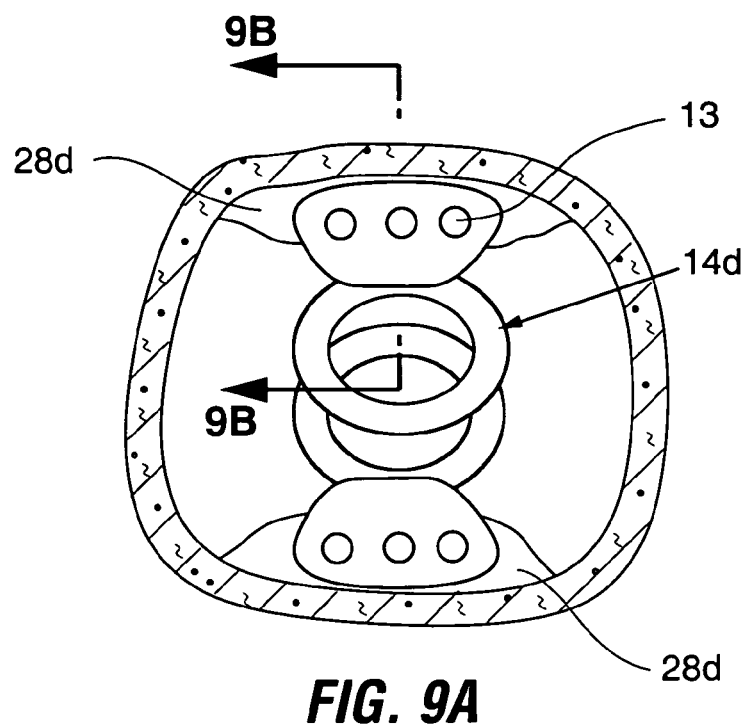
FIG. 9A is a cross-sectional view similar to FIG. 4A showing use of a third alternative embodiment of an anchor. Two such anchors are shown connected to two plications formed in the stomach wall.
Figure 9B:
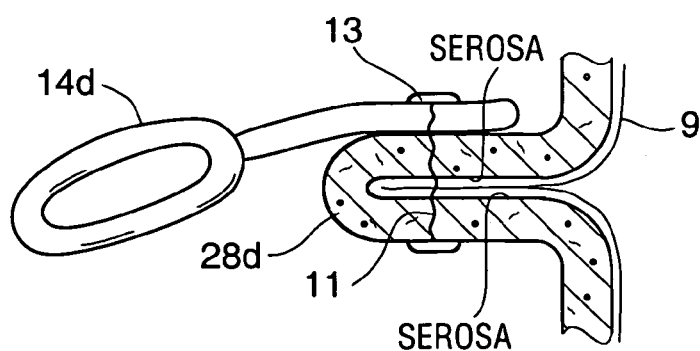
FIG. 9B is a cross-sectional side view taken along the plan designed 9B-9B in FIG. 9A.

FIGS. 9A and 9B illustrate an alternative method for implanting anchors 14d. According to this method, anchors 14d are attached to tissue plications 28d formed in the stomach wall. Various methods for forming plications are described in WO 2005/037152, entitled "Devices and Methods for Retaining a Gastro-Esophageal Implant" published Apr. 25, 2002. According to one method of forming a serosal plication, tissue within the stomach interior is pinched together (using an endoscopic grasper, for example) to pinch serosal layers on the stomach exterior into contact with one another, thereby forming folded tissue tab as shown. A reinforcing patch 9 may be positioned between the serosal tissue layers. The patch may function as scaffolding that promotes tissue ingrowth and/or function to reinforce the adhesions that form. Sutures 11 (which may be bioabsorbable), pledgets 13, t-bars or other fastening means are used to hold the tissue layers together at least until adhesions bond the tissue layers together. These fasteners may also be used to attach the anchors 14*d* to the plication as shown, although in an alternative method the anchors 14*d* are coupled to the plications 28*d* using sutures, staples or other fasteners after the plications have healed.

Eventually, adhesions form between the tissue layers (and through and/or onto the interstices of the patch) and serve to reinforce the bond between the tissue layers.

The patch may be a synthetic or non-synthetic mesh, porous material, slotted material, or any other material through which adhesions will form or onto which tissue will grow. Examples include, but are not limited to, polypropylene, materials sold under the trade names Goretex or Dacron, or tissue graft material such as the Surgisis material sold by Wilson Cook Medical, Inc. The material may be treated with tissue-ingrowth promoting substances such as biologics.

Figure 15:
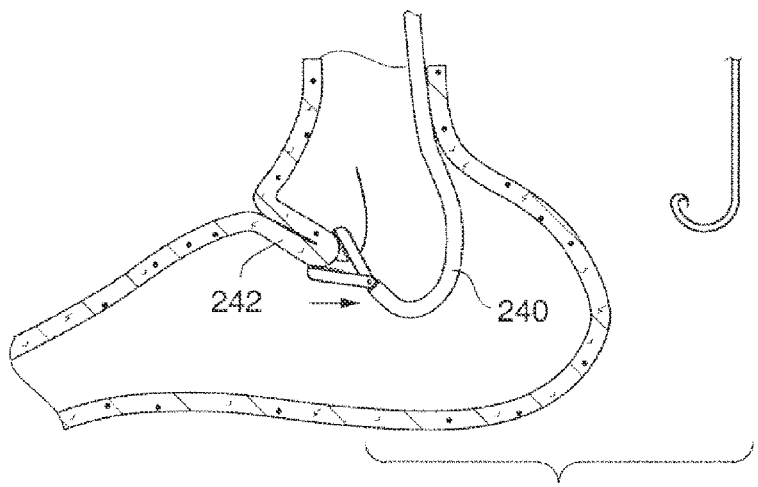
FIGS. 15A through 15D are a sequence of cross-section views of a stomach illustrating a method of re-shaping tissue to form a circumferential plication, and using the circumferential plication to retain an implant.
Figure 15:
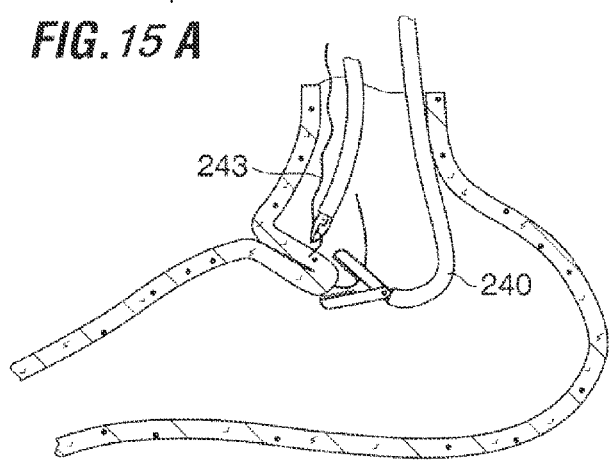
Figure 15:
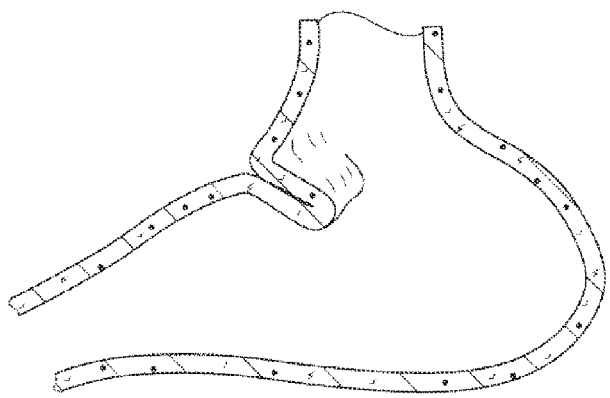
Figure 15D:
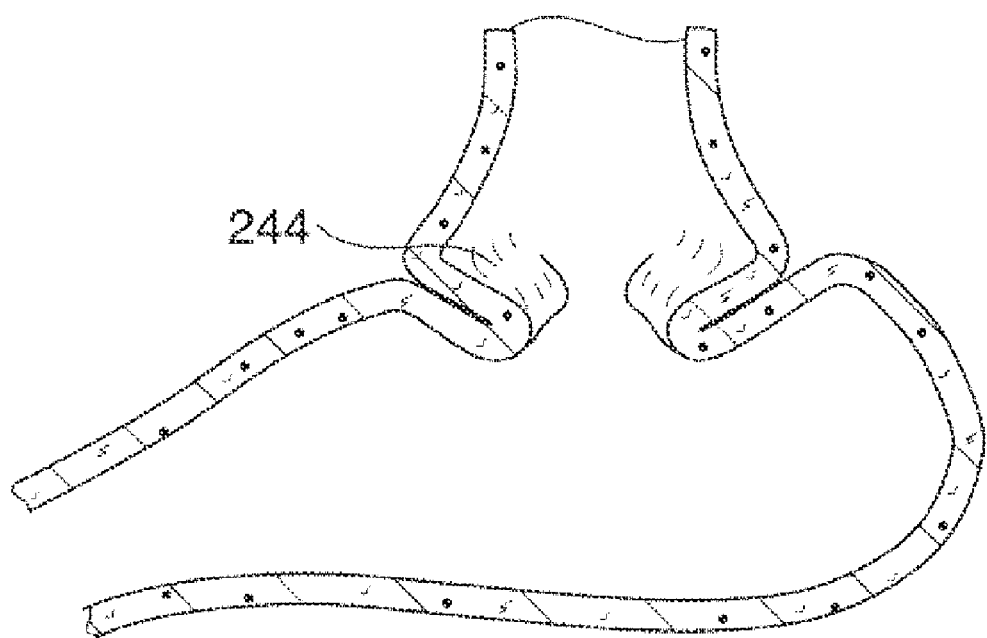

FIGS. 15A through 15D illustrate another method in which the stomach wall may be re-shaped for retention of an implant. According to this method, a circumferential ridge of tissue may be formed around the interior stomach wall, such as at the gastro-esophageal junction region, and the circumferential ridge may be used to retain the implant. Referring to FIG. 15B, a serosal plication may be formed by engaging a region of the interior stomach wall using an endoscopic grasper 240, hook, pronged instrument, or similar device. By pulling the engaged wall region inwardly, sections of external serosal tissue are drawn into contact with one another to form serosa-to-serosal plication 242 (FIG. 15D). With the plication engaged by the endoscopic instrument, a suture 243, staple or other fastener is passed through the plication 242 as shown in FIG. 15B to retain the plication. A plurality of the plications 242 are formed around the interior circumference of the stomach, thus creating a circumferential ridge 244 of plicated tissue encircling the wall of the stomach. Over time, the opposed serosal layers form an adhesion. A restrictive implant 246 is then positioned in the stomach, proximally of the ridge 244.

Attachment of the implant 246 may be performed during the same procedure in which the circumferential ridge is formed, or at a later date to permit the adhesions to form before the ridge is subjected to the stresses that will be imparted against it by the implant.

Figure 16:
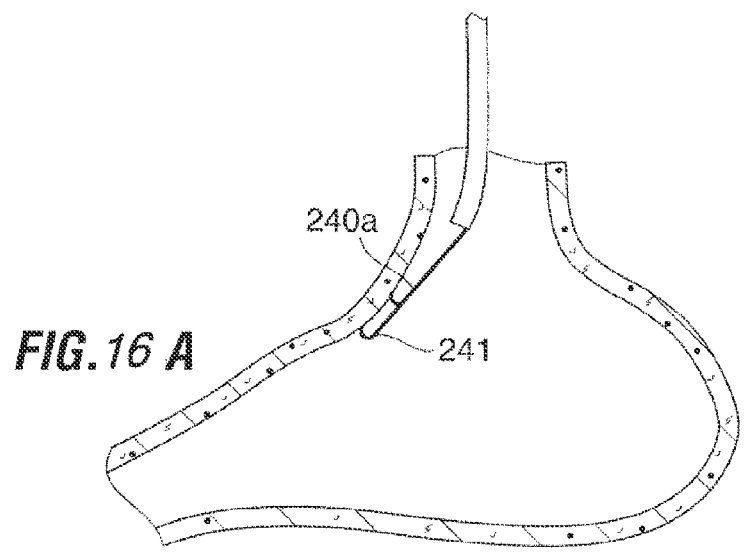
FIGS. 16A through 16C are a sequence of cross-section views illustrating a modification to the method shown in FIGS. 15A through 15D.
Figure 16:
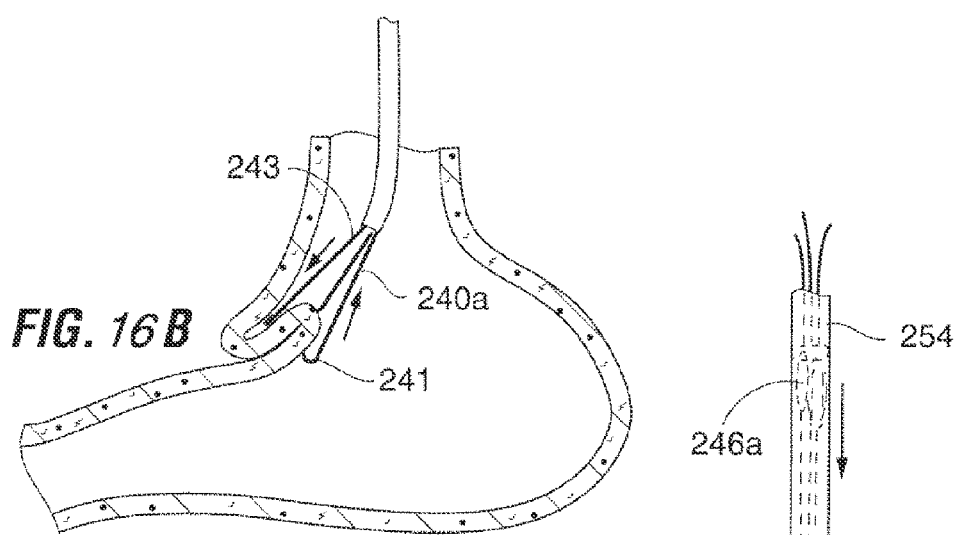
Figure 16:
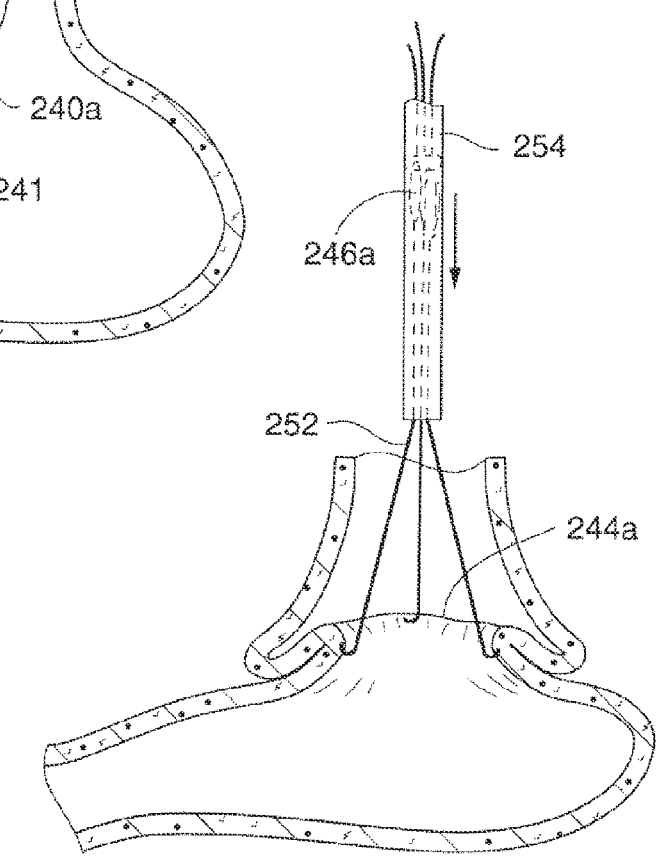

FIGS. 16A through 16C illustrate a slightly modified method for using serosal-to-serosal plication of wall tissue to form a circumferential ridge, and for securing an implant to the ridge. Referring to FIGS. 16A and 16B, tissue is plicated using an endoscopic instrument 240*a* which includes prong members 241. To form a plication, prong members 241 are used to pull stomach wall tissue in a proximal direction while a suture needle 243 or other fastening instrument advanced distally to drive sutures, t-bars, rivets or other fasteners downwardly into the plicated tissue as shown in FIG. 16B. Force dissipating elements such as pledgets may be used to dissipate forces against the tissue surface.

Referring to FIG. 16C, a few (for example two to four) such plications are formed around the wall to form a circumferential ridge 244*a* (FIG. 16C).

Implant Positioning

Figure 10A:
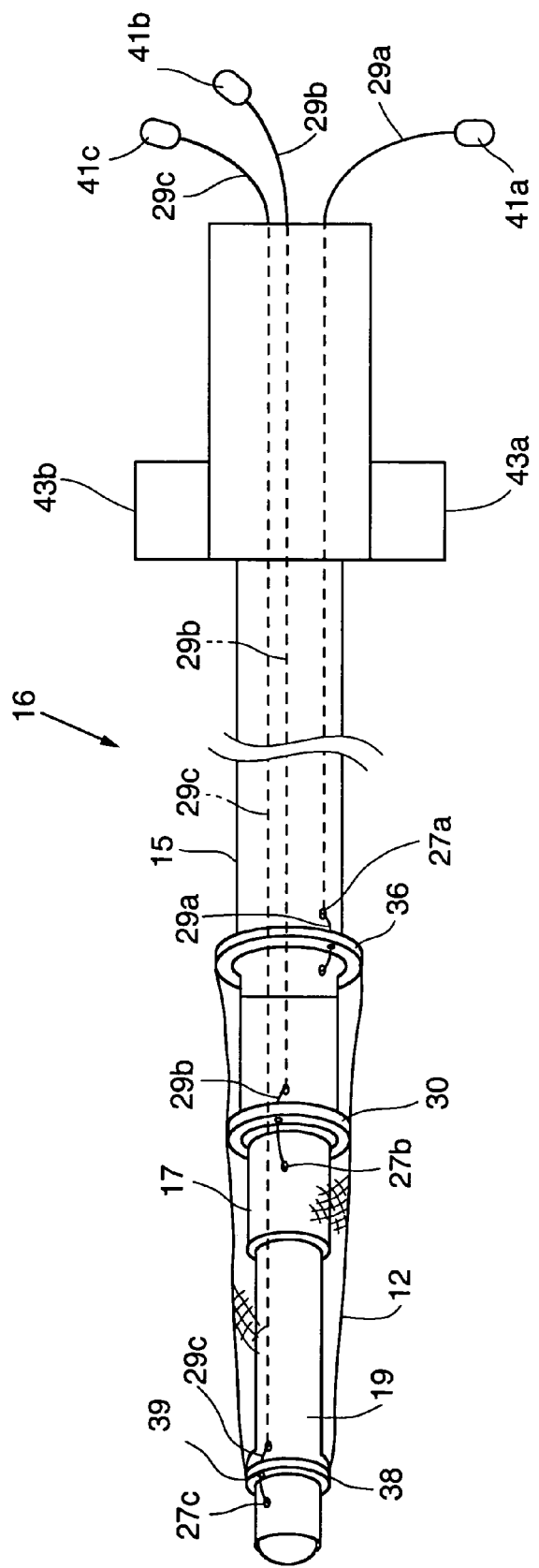

FIG. 10A illustrates one method of mounting the implant 12 to the tool 16 in preparation for implantation. In this figure, the implant walls are shown as transparent so that the orad and aborad rings 36, 38 and the waist ring 30 can be seen. In a preferred method, the implant is attached to the tool at three attachment points which fall at the orad ring, the aborad ring, and the waist section. In alternative methods the implant may be attached at different locations, such as only the aborad or orad ends of the device, or elsewhere.

To mount the implant according to the method of FIG. 10A, a first retention element such as nitinol wire 29*a* is introduced into an opening at the open proximal end of the tool and passed distally through the lumen of the inner shaft 19. The distal end of the wire is then extended through the distalmost one of the holes 27*c*, through opening 39 in the aborad ring 38, then inserted back into the lumen of the inner shaft and returned to the proximal end of the tool 16 and may be marked and held together by a tab 41*c*. The two ends of the wire 29*c* are retained outside the tool. Similarly, a second nitinol wire 29*b* is passed down the annular space between the inner shaft 19 and the middle shaft 17, passed out of the middle shaft through one of the openings 27*b*, then through opening 31 in the waist ring 30 of the implant and back into the annular space via the most proximal one of the openings 27*b*. The ends of the wire 29*b* are retained by a tab 41*b*. This process is repeated at the orad end of the implant to anchor the orad ring 36 using nitinol wire 29*a*. The relative positions of the shafts 15, 17, 19 are adjusted to place the implant 12 in the elongated position, and then locked in place.

Figure 10B:
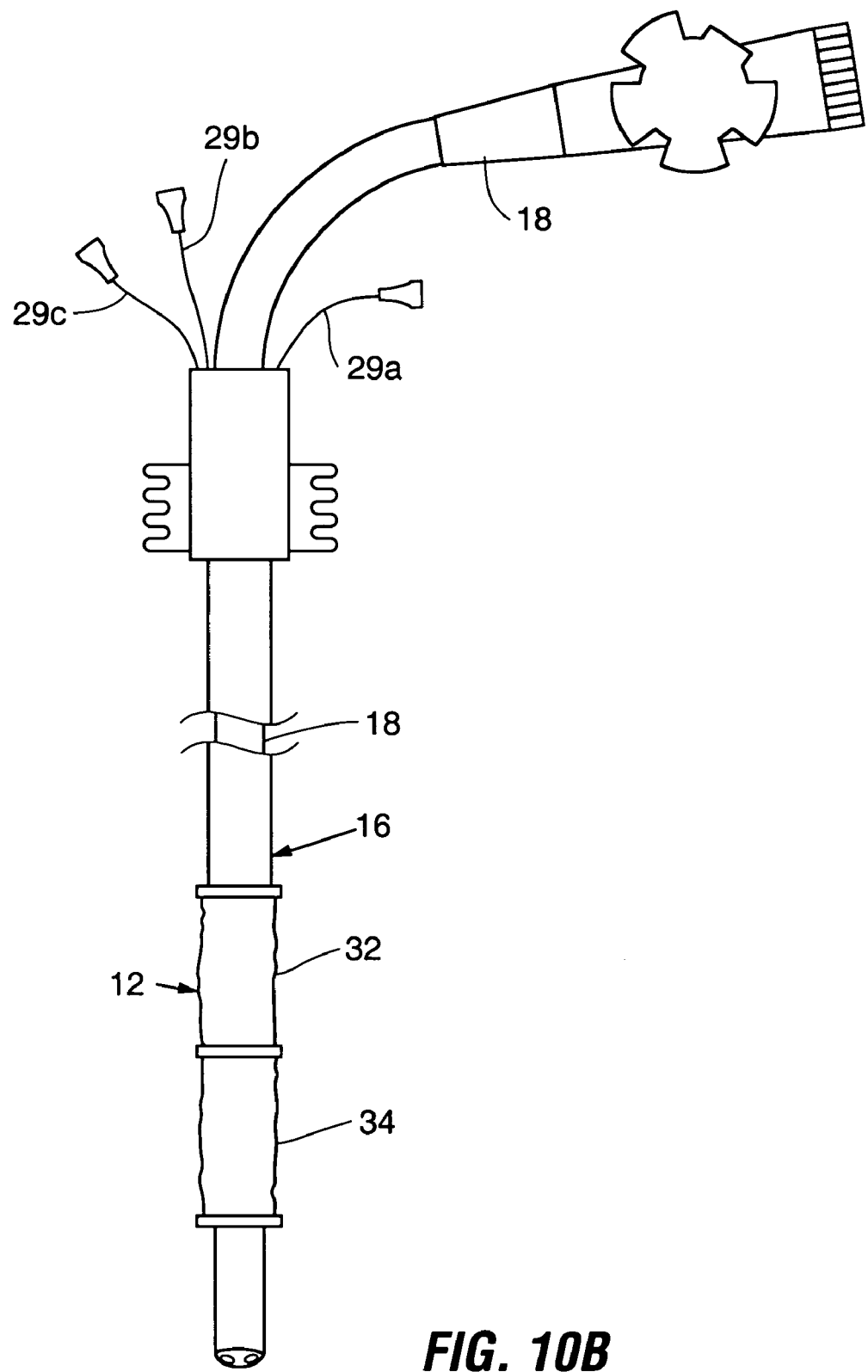

Referring to FIG. 10B, once the implant 12 is assembled onto the implant tool 16, the tool 16 is positioned over the endoscope 18 by sliding the endoscope through the central lumen of the tool's inner shaft 19. Next, the distal end of the endoscope is passed orally into the esophagus, and then through the loops 22 of the anchors 14 previously implanted. The endoscope is retroflexed as shown in FIG. 10C, allowing the surgeon to visually confirm that the endoscope has passed through both loops.

Referring to FIG. 10D, the implant tool 16 is advanced over the endoscope until the waist 30 of the implant 12 is adjacent to the loops 22. The waist of the implant may be marked with identifying markers to simplify this step of the procedure. Once the waist 30 is properly positioned, release tab 43*a* is depressed to allow the outer shaft 15 of the implant tool 16 is slide distally, causing the orad ring 36 to move closer to the waist 30 thus expanding orad section 32 of the implant as shown in FIG. 10E. Once it is visually confirmed that the expanded orad portion of the implant is properly positioned, wire 29*a* is withdrawn to disconnect the orad ring 36 from the implant tool 16.

Figure 10F:
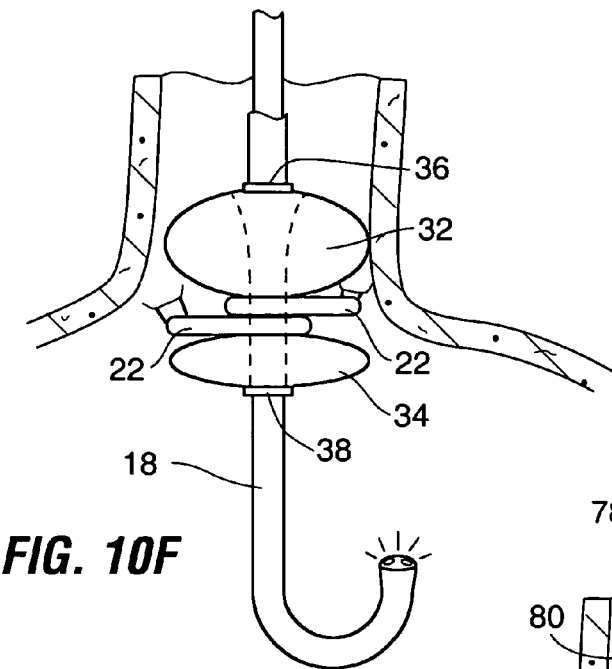

Next, referring to FIG. 10F, the release tab 43*b* is activated to allow the inner shaft 19 to be withdrawn in a proximal direction, bringing the aborad ring 38 closer to the waist 30 and allowing the aborad portion 34 of the implant to expand. Proper deployment is visually confirmed, and then the wires 29*b* and 29*c* are withdrawn to detach the implant 12 from the tool 16.

Removal

Figure 11A:
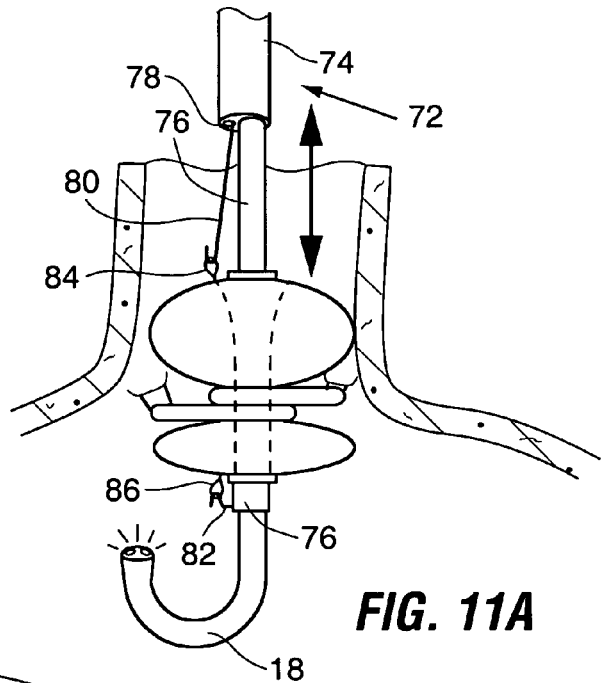
FIGS. 11A and 11C are a sequence of drawings illustrating use of the system of FIG. 2 to remove an implant.
Figure 11B:
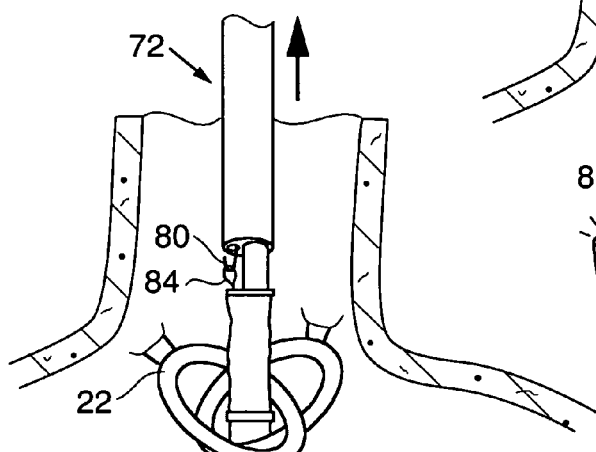

FIGS. 11A and 11B illustrate one example of a method for removing the implant 12. According to the method of FIGS. 11A and 11B, removal is carried out using an extraction tool 72 comprised of a sheath 74 and a hollow rod 76 telescopically disposed within the sheath 74. Endoscope 18 is slidable through the lumen of the hollow rod 76.

Sheath 74 includes a small side lumen 78. An elongate wire having a hook 80 at its distal end is extendable through the side lumen 78 to deploy the hook 80 from the distal end of the sheath 74. Another hook 82 is positioned on the distal end of the hollow rod.

Initially, the extraction tool 72 is arranged with the hollow rod 76 fully withdrawn into the sheath 74, but with the endoscope 18 extending distally from the distal end of the sheath 74. The tool 72 is introduced into the esophagus such that the sheath 74 is positioned proximally of the implant 12. The endoscope 18 is advanced through the implant 12 and retroflexed as shown in FIG. 11A to permit visualization of the procedure.

Figure 11C:
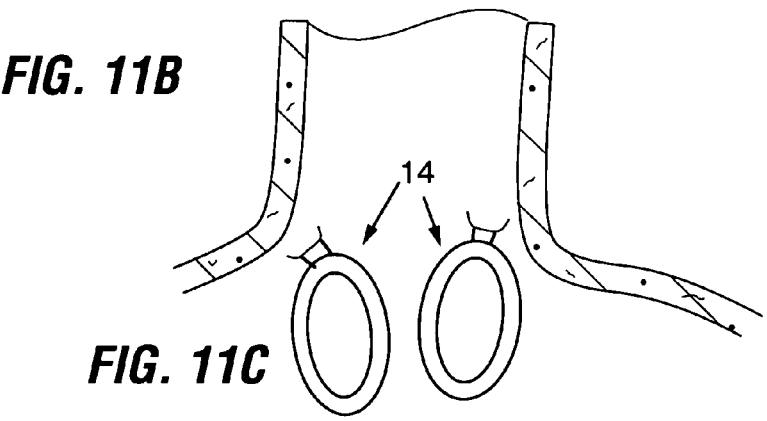

Next, hook 80 is advanced through sheath 74 and manipulated to ensnare a retrieval loop 84 on the orad portion of the implant 12. Alternatively, the hook 80 may be used to grasp the orad ring 36 (FIG. 2) of the implant. Once the orad portion of the implant has been engaged, hollow rod 76 is advanced to allow hook 82 to capture a retrieval loop 86 on the aborad end of the implant 12 (or to capture the aborad ring 38). The hollow rod 76 and sheath 74 are moved in opposite directions to elongate the implant 12 as shown in FIG. 11B, and are then simultaneously withdrawn from the stomach (along with the endoscope 18) while maintaining the implant in the elongated position. Once the implant 12 has been explanted, only the anchors 14 remain in place as shown in FIG. 11C.

Alternative Configuration

Figure 12:
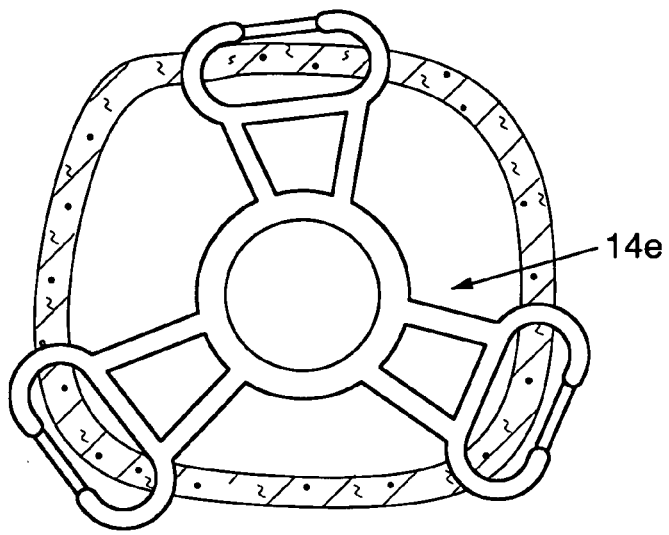
FIG. 12 is a cross-section view similar to FIG. 4A illustrating a fourth alternative anchor embodiment.

FIG. 12 illustrates an alternative anchor 14e which may be used to support an implant. Anchor 14e may be a single component or multiple components arranged to form a web-like structure in a gastro-esophageal junction. As discussed with other anchor embodiments, the anchor 14e is preferably linked to tissue tunnels 28, although it may alternatively be coupled to serosal plications as discussed in connection with FIGS. 9A and 9B, or it may be attached to the tissue in other ways.

Figure 13:
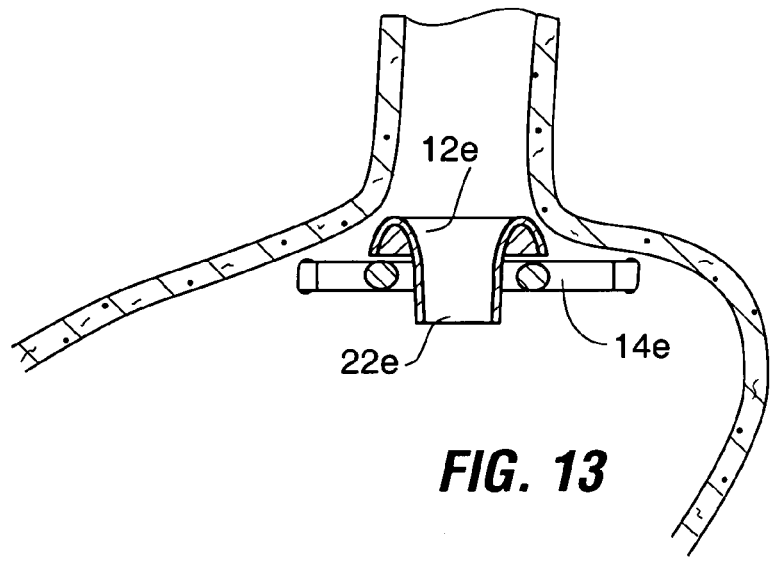
FIG. 13 illustrates use of the anchor of FIG. 12 to support an implant.
Figure 14:
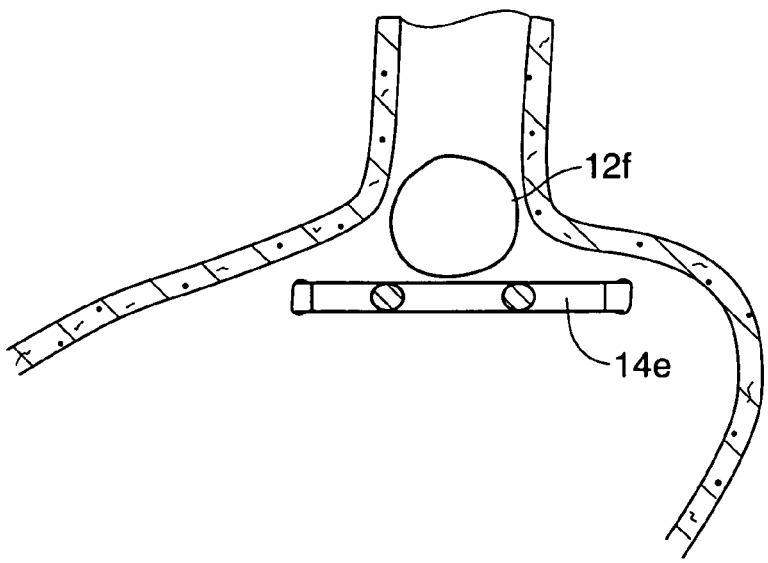
FIG. 14 illustrates use of the anchor of FIG. 12 to support an alternative implant.

Referring to FIGS. 13, anchor 14e may include a loop 22e for receiving an implant 12e as described above in connection with other embodiments. The implant 12e may have an hourglass shape defined by a central waist section as with implant 12 of FIG. 2, or it may be tapered as shown in FIG. 13. Referring to FIG. 14, the anchor 14e may also be used to support an implant 12f by simply preventing the implant 12f from descending further into the gastrointestinal tract. For example, the implant 12f may take the form of a space occupying balloon that is not physically attached or coupled to the anchor 14e.

Implantation of the anchor 14e may be accomplished using techniques described above. The implant 12f may be positioned by coupling an inflation tube to an inflation port in the implant 12f, and then passing the implant 12f down a sheath positioned in the esophagus. Once the implant is within the stomach, the inflation tube is used to inflate the implant 12f, and is then detached from the implant and withdrawn from the body.

The implant 12e may be implanted using a methodology similar to that described in the Implantation section.

Various components and methods have been described herein. These embodiments are given by way of example and are not intended to limit the scope of the present invention. It will be apparent to persons skilled in the relevant art that various changes in form and detail may be made therein without departing from the spirit and scope of the invention. This is especially true in light of technology and terms within the relevant art(s) that may be later developed.

It should be appreciated, moreover, that the various features of the embodiments that have been described might be combined in various ways to produce numerous additional embodiments. Also, while various materials, dimensions, shapes, implantation locations, etc. have been described for use with disclosed embodiments, others besides those disclosed may be utilized without exceeding the scope of the invention. For example, the anchoring methods and devices are not limited to use within the gastro-intestinal system and may be used for implants placed elsewhere in the body.

Any and all patents, patent applications and printed publications referred to above are incorporated by reference.

What is claimed is:

1. A method of securing a food-restrictor device near the gastroesophageal junction within the interior of the stomach in a subject, comprising the steps of:
    forming a plurality of plications arrayed at spaced-apart positions about the gastroesophageal junction within the stomach and forming a tissue tunnel extending through each plication;
    placing a plurality of staples around the tunnel to hold the plication together in the region of the tissue tunnel,
    after forming said tissue tunnel and placing said staples around the tunnel, coupling to each plication, an anchor having a fastener with first and second ends, by extending the first fastener end through the tissue tunnel and engaging the first and second ends; and
    securing the food-restrictor device within the stomach by attaching the food-restrictor device to each anchor.

2. The method of claim 1, wherein the food-restrictive device is a pouch for restricting food intake into the stomach and said attaching results in a proximal opening of the pouch being aligned with the esophagus.

3. The method of claim 1, wherein forming a plurality of plications comprises forming three plications arrayed at spaced-apart positions.

4. The method of claim 1, wherein forming a plurality of plications comprises forming four plications arrayed at spaced-apart positions.

* * * * *